(12) United States Patent
Unger

(10) Patent No.: US 9,918,782 B2
(45) Date of Patent: *Mar. 20, 2018

(54) ENDOSCOPIC VESSEL SEALER AND DIVIDER FOR LARGE TISSUE STRUCTURES

(71) Applicant: COVIDIEN LP, Mansfield, MA (US)

(72) Inventor: Jeffrey R. Unger, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 397 days.

This patent is subject to a terminal disclaimer.

(21) Appl. No.: 14/806,211

(22) Filed: Jul. 22, 2015

(65) Prior Publication Data

US 2015/0351829 A1    Dec. 10, 2015

Related U.S. Application Data

(60) Division of application No. 13/663,317, filed on Oct. 29, 2012, now Pat. No. 9,113,903, which is a division
(Continued)

(51) Int. Cl.
*A61B 18/12* (2006.01)
*A61B 18/14* (2006.01)
(Continued)

(52) U.S. Cl.
CPC .......... *A61B 18/1445* (2013.01); *A61B 17/32* (2013.01); *A61B 18/1442* (2013.01);
(Continued)

(58) Field of Classification Search
CPC . A61B 17/32; A61B 18/1442; A61B 18/1445; A61B 2017/2945;
(Continued)

(56) References Cited

U.S. PATENT DOCUMENTS 371,664 A    10/1887  Brannan et al.
702,472 A     6/1902  Pignolet
(Continued)

FOREIGN PATENT DOCUMENTS

CA    2104423 A1    2/1994
CA    2561622 A1    3/2007
(Continued)

OTHER PUBLICATIONS

Int'l Search Report EP 98957771 dated Aug. 9, 2001.
(Continued)

*Primary Examiner* — Daniel Fowler

(57) ABSTRACT

An endoscopic bipolar forceps includes a housing having a shaft affixed thereto, the shaft including jaw members at a distal end thereof. The forceps also includes a drive assembly which moves the jaw member relative to one another for manipulating tissue and a knife assembly for cutting tissue disposed between jaw members. The forceps also includes a knife lockout mechanism operatively connected to the drive assembly. Movement of the drive assembly moves the knife lockout mechanism from a first orientation in obstructive relationship with the knife bar to prevent movement thereof to a second position which allows selective, unencumbered movement of the knife assembly to cut tissue disposed between the jaw members.

14 Claims, 30 Drawing Sheets

Related U.S. Application Data of application No. 12/410,188, filed on Mar. 24, 2009, now Pat. No. 8,298,232, which is a continuation-in-part of application No. 11/595,194, filed on Nov. 9, 2006, now Pat. No. 7,766,910.

(60) Provisional application No. 61/040,048, filed on Mar. 27, 2008, provisional application No. 60/761,442, filed on Jan. 24, 2006.

(51) Int. Cl.
  *A61B 17/32* (2006.01)
  *A61B 17/29* (2006.01)
  *A61B 18/00* (2006.01)
  *A61B 18/18* (2006.01)
  *A61B 90/00* (2016.01)

(52) U.S. Cl.
  CPC .......... *A61B 2017/2945* (2013.01); *A61B 2018/0063* (2013.01); *A61B 2018/00404* (2013.01); *A61B 2018/00601* (2013.01); *A61B 2018/00916* (2013.01); *A61B 2018/1412* (2013.01); *A61B 2018/1432* (2013.01); *A61B 2018/1455* (2013.01); *A61B 2018/1861* (2013.01); *A61B 2090/034* (2016.02)

(58) Field of Classification Search
  CPC  A61B 2018/00404; A61B 2018/00601; A61B 2018/0063; A61B 2018/00916; A61B 2018/1412; A61B 2018/1432; A61B 2018/1455; A61B 2018/1861
  See application file for complete search history.

(56) References Cited

U.S. PATENT DOCUMENTS

| | | |
|---|---|---|
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,279,753 A | 4/1942 | Knopp |
| 2,305,156 A | 12/1942 | Grubel |
| 2,327,353 A | 8/1943 | Karle |
| 2,632,661 A | 3/1953 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| D249,549 S | 9/1978 | Pike |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Koch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| D298,353 S | 11/1988 | Manno |
| D299,413 S | 1/1989 | DeCarolis |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyarna et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |

(56) References Cited

U.S. PATENT DOCUMENTS

| | | |
|---|---|---|
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| D343,453 S | 1/1994 | Noda |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,312,433 A | 5/1994 | Boebel et al. |
| 5,313,027 A | 5/1994 | Inoue et al. |
| 5,314,445 A | 5/1994 | Heidmueller Nee Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| D349,341 S | 8/1994 | Lichtman et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| D354,564 S | 1/1995 | Medema |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| D358,887 S | 5/1995 | Feinberg |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,512,721 A | 4/1996 | Young et al. |
| 5,514,134 A | 5/1996 | Rydell et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |

(56) References Cited

U.S. PATENT DOCUMENTS

| | | |
|---|---|---|
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | Lemaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,762,255 A | 6/1998 | Chrisman et al. |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,646 A | 7/1998 | Koblish et al. |
| 5,779,701 A | 7/1998 | McBrayer et al. |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,083 A | 10/1998 | Shemesh et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| D402,028 S | 12/1998 | Grimm et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| D408,018 S | 4/1999 | McNaughton |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Austin et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| D416,089 S | 11/1999 | Barton et al. |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka |
| 6,017,358 A | 1/2000 | Yoon et al. |
| 6,021,693 A | 2/2000 | Feng-Sing |
| 6,024,741 A | 2/2000 | Williamson, IV et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |

(56) References Cited

U.S. PATENT DOCUMENTS

| | | |
|---|---|---|
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | Van De Moer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan, Jr. |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| D453,923 S | 2/2002 | Olson |
| 6,345,532 B1 | 2/2002 | Coudray et al. |
| 6,350,264 B1 | 2/2002 | Hooven |
| D454,951 S | 3/2002 | Bon |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| D465,281 S | 11/2002 | Lang |
| D466,209 S | 11/2002 | Bon |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | de Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |

(56) References Cited

U.S. PATENT DOCUMENTS

| | | |
|---|---|---|
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| D502,994 S | 3/2005 | Blake, III |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,274 S | 12/2006 | Visconti et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| D538,932 S | 3/2007 | Malik |
| 7,195,631 B2 | 3/2007 | Dumbauld |
| D541,418 S | 4/2007 | Schechter et al. |
| 7,207,990 B2 | 4/2007 | Lands et al. |
| D541,611 S | 5/2007 | Aglassinger |
| D541,938 S | 5/2007 | Kerr et al. |
| 7,223,264 B2 | 5/2007 | Daniel et al. |
| 7,223,265 B2 | 5/2007 | Keppel |
| D545,432 S | 6/2007 | Watanabe |
| 7,232,440 B2 | 6/2007 | Dumbauld et al. |
| D547,154 S | 7/2007 | Lee |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelton, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |

(56) References Cited

U.S. PATENT DOCUMENTS

| | | |
|---|---|---|
| D627,462 S | 11/2010 | Kingsley |
| D628,289 S | 11/2010 | Romero |
| D628,290 S | 11/2010 | Romero |
| D630,324 S | 1/2011 | Reschke |
| 8,016,827 B2 | 9/2011 | Chojin |
| D649,249 S | 11/2011 | Guerra |
| D649,643 S | 11/2011 | Allen, IV et al. |
| 8,114,122 B2 | 2/2012 | Nau, Jr. |
| 8,142,473 B2 | 3/2012 | Cunningham |
| 8,162,973 B2 | 4/2012 | Cunningham |
| D661,394 S | 6/2012 | Romero et al. |
| 8,197,479 B2 | 6/2012 | Olson et al. |
| 8,226,650 B2 | 7/2012 | Kerr |
| 8,251,994 B2 | 8/2012 | McKenna et al. |
| 8,257,387 B2 | 9/2012 | Cunningham |
| 8,282,634 B2 | 10/2012 | Cunningham et al. |
| 8,303,582 B2 | 11/2012 | Cunningham |
| 8,317,787 B2 | 11/2012 | Hanna |
| 8,328,803 B2 | 12/2012 | Regadas |
| 8,382,792 B2 | 2/2013 | Chojin |
| 8,454,602 B2 | 6/2013 | Kerr et al. |
| 8,469,956 B2 | 6/2013 | McKenna et al. |
| 8,469,957 B2 | 6/2013 | Roy |
| 8,486,107 B2 | 7/2013 | Hinton |
| 8,523,898 B2 | 9/2013 | Bucciaglia et al. |
| 8,529,566 B2 | 9/2013 | Kappus et al. |
| 8,535,312 B2 | 9/2013 | Horner |
| 8,568,408 B2 | 10/2013 | Townsend et al. |
| 8,591,510 B2 | 11/2013 | Allen, IV et al. |
| 8,623,276 B2 | 1/2014 | Schmaltz et al. |
| 8,628,557 B2 | 1/2014 | Collings et al. |
| 8,632,539 B2 | 1/2014 | Twomey et al. |
| 8,632,564 B2 | 1/2014 | Cunningham |
| 8,636,761 B2 | 1/2014 | Cunningham et al. |
| 8,679,098 B2 | 3/2014 | Hart |
| 8,679,140 B2 | 3/2014 | Butcher |
| 8,685,009 B2 | 4/2014 | Chernov et al. |
| 8,685,056 B2 | 4/2014 | Evans et al. |
| 8,696,667 B2 | 4/2014 | Guerra et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,413 B2 | 6/2014 | Dycus |
| 8,747,434 B2 | 6/2014 | Larson et al. |
| 8,752,264 B2 | 6/2014 | Ackley et al. |
| 8,756,785 B2 | 6/2014 | Allen, IV et al. |
| 8,764,748 B2 | 7/2014 | Chojin |
| 8,784,417 B2 | 7/2014 | Hanna |
| 8,795,274 B2 | 8/2014 | Hanna |
| 8,845,636 B2 | 9/2014 | Allen, IV et al. |
| 8,852,185 B2 | 10/2014 | Twomey |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,900,232 B2 | 12/2014 | Ourada |
| 8,920,461 B2 | 12/2014 | Unger et al. |
| 8,939,972 B2 | 1/2015 | Twomey |
| 8,961,513 B2 | 2/2015 | Allen, IV et al. |
| 8,961,514 B2 | 2/2015 | Garrison |
| 8,961,515 B2 | 2/2015 | Twomey et al. |
| 8,968,283 B2 | 3/2015 | Kharin |
| 8,968,298 B2 | 3/2015 | Twomey |
| 8,968,305 B2 | 3/2015 | Dumbauld et al. |
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,113,903 B2 | 8/2015 | Unger |
| 2002/0107517 A1 | 8/2002 | Witt et al. |
| 2002/0111624 A1 | 8/2002 | Witt et al. |
| 2003/0014052 A1 | 1/2003 | Buysse et al. |
| 2003/0014053 A1 | 1/2003 | Nguyen et al. |
| 2003/0018332 A1 | 1/2003 | Schmaltz et al. |
| 2003/0069570 A1 | 4/2003 | Witzel et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0115296 A1 | 6/2004 | Duffin |
| 2004/0143263 A1 | 7/2004 | Schechter et al. |
| 2004/0148035 A1 | 7/2004 | Barrett et al. |
| 2004/0162557 A1 | 8/2004 | Tetzlaff et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0236326 A1 | 11/2004 | Schulze et al. |
| 2004/0249374 A1 | 12/2004 | Tetzlaff et al. |
| 2004/0260281 A1 | 12/2004 | Baxter et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101952 A1 | 5/2005 | Lands et al. |
| 2005/0149017 A1 | 7/2005 | Dycus |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0052778 A1 | 3/2006 | Chapman et al. |
| 2006/0052779 A1 | 3/2006 | Hammill |
| 2006/0064086 A1 | 3/2006 | Odom |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |

(56) References Cited

U.S. PATENT DOCUMENTS

| | | |
|---|---|---|
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |
| 2009/0234354 A1 | 9/2009 | Johnson et al. |
| 2009/0248021 A1 | 10/2009 | McKenna |
| 2010/0042143 A1 | 2/2010 | Cunningham |
| 2010/0049187 A1 | 2/2010 | Carlton et al. |
| 2010/0057081 A1 | 3/2010 | Hanna |
| 2010/0063500 A1 | 3/2010 | Muszala |
| 2010/0069903 A1 | 3/2010 | Allen, IV et al. |
| 2010/0069953 A1 | 3/2010 | Cunningham et al. |
| 2010/0076427 A1 | 3/2010 | Heard |
| 2010/0076430 A1 | 3/2010 | Romero |
| 2010/0076431 A1 | 3/2010 | Allen, IV |
| 2010/0280515 A1 | 11/2010 | Hixson et al. |
| 2012/0239034 A1 | 9/2012 | Homer et al. |
| 2012/0259331 A1 | 10/2012 | Garrison |
| 2012/0265241 A1 | 10/2012 | Hart et al. |
| 2012/0296205 A1 | 11/2012 | Chemov et al. |
| 2012/0296238 A1 | 11/2012 | Chemov et al. |
| 2012/0296239 A1 | 11/2012 | Chemov et al. |
| 2012/0296317 A1 | 11/2012 | Chemov et al. |
| 2012/0296323 A1 | 11/2012 | Chemov et al. |
| 2012/0296324 A1 | 11/2012 | Chemov et al. |
| 2012/0296371 A1 | 11/2012 | Kappus et al. |
| 2012/0303025 A1 | 11/2012 | Garrison |
| 2012/0303026 A1 | 11/2012 | Dycus et al. |
| 2012/0310240 A1 | 12/2012 | Olson et al. |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chemov et al. |
| 2013/0018372 A1 | 1/2013 | Sims et al. |
| 2013/0022495 A1 | 1/2013 | Allen, IV et al. |
| 2013/0046295 A1 | 2/2013 | Kerr et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079774 A1 | 3/2013 | Whitney et al. |
| 2013/0085491 A1 | 4/2013 | Twomey et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0138101 A1 | 5/2013 | Kerr |
| 2013/0138129 A1 | 5/2013 | Garrison et al. |
| 2013/0144284 A1 | 6/2013 | Behnke, II et al. |
| 2013/0178852 A1 | 7/2013 | Allen, IV et al. |
| 2013/0185922 A1 | 7/2013 | Twomey et al. |
| 2013/0197503 A1 | 8/2013 | Orszulak |
| 2013/0253489 A1 | 9/2013 | Nau, Jr. et al. |
| 2013/0255063 A1 | 10/2013 | Hart et al. |
| 2013/0274736 A1 | 10/2013 | Garrison |
| 2013/0289561 A1 | 10/2013 | Waaler et al. |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0325057 A1 | 12/2013 | Larson et al. |
| 2014/0005663 A1 | 1/2014 | Heard et al. |
| 2014/0005666 A1 | 1/2014 | Moua et al. |

FOREIGN PATENT DOCUMENTS

| | | |
|---|---|---|
| CN | 201299462 | 9/2009 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 20 2007 009317 U1 | 8/2007 |
| DE | 202007009165 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 0467501 A1 | 1/1992 |
| EP | 0541930 A1 | 5/1993 |
| EP | 0572131 A1 | 12/1993 |
| EP | 0584787 A1 | 3/1994 |
| EP | 0589555 A1 | 3/1994 |
| EP | 0589453 A3 | 4/1994 |

(56) References Cited

FOREIGN PATENT DOCUMENTS

| | | |
|---|---|---|
| EP | 0624348 A3 | 6/1995 |
| EP | 0364216 B1 | 1/1996 |
| EP | 0518230 B1 | 5/1996 |
| EP | 0517243 B1 | 9/1997 |
| EP | 0878169 A1 | 11/1998 |
| EP | 0623316 B1 | 3/1999 |
| EP | 0650701 B1 | 3/1999 |
| EP | 0923907 A1 | 6/1999 |
| EP | 0640317 B1 | 9/1999 |
| EP | 0986990 A1 | 3/2000 |
| EP | 1034747 A1 | 9/2000 |
| EP | 1034748 | 9/2000 |
| EP | 0694290 B1 | 11/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1177771 | 2/2002 |
| EP | 1159926 A3 | 3/2003 |
| EP | 0717966 B1 | 4/2003 |
| EP | 1301135 | 4/2003 |
| EP | 0887046 B1 | 7/2003 |
| EP | 1330991 A1 | 7/2003 |
| EP | 1486177 | 6/2004 |
| EP | 1472984 | 11/2004 |
| EP | 0754437 B2 | 12/2004 |
| EP | 1025807 B1 | 12/2004 |
| EP | 0774232 B1 | 1/2005 |
| EP | 0853922 B1 | 2/2005 |
| EP | 1527747 | 5/2005 |
| EP | 1530952 | 5/2005 |
| EP | 1532932 A1 | 5/2005 |
| EP | 1535581 | 6/2005 |
| EP | 1609430 A1 | 12/2005 |
| EP | 1034746 B1 | 3/2006 |
| EP | 1632192 | 3/2006 |
| EP | 1642543 | 4/2006 |
| EP | 1645238 A1 | 4/2006 |
| EP | 1645240 A2 | 4/2006 |
| EP | 1649821 | 4/2006 |
| EP | 0875209 B1 | 5/2006 |
| EP | 1707143 A1 | 10/2006 |
| EP | 1769765 A1 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2213416 A | 8/1989 |
| GB | 2214430 A | 9/1989 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 | 9/1999 |
| JP | 2000-102545 A | 4/2000 |
| JP | 2000342599 A | 12/2000 |
| JP | 2060350732 | 12/2000 |
| JP | 2001-8944 | 1/2001 |
| JP | 2001-29356 | 2/2001 |
| JP | 2001128990 A | 5/2001 |
| JP | 2001-190564 A | 7/2001 |
| JP | 2001-3400 | 11/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2007098139 A | 4/2007 |
| JP | 2007195982 A | 8/2007 |
| JP | 2011125195 A | 6/2011 |
| SU | 401367 A1 | 10/1973 |
| WO | 00/24330 | 5/2000 |
| WO | 00/24331 | 5/2000 |
| WO | 0036986 A1 | 6/2000 |
| WO | 00/41638 | 7/2000 |
| WO | 00/47124 | 8/2000 |
| WO | 00/53112 | 9/2000 |
| WO | 0059392 A1 | 10/2000 |
| WO | 01/17448 | 3/2001 |
| WO | 0115614 A1 | 3/2001 |
| WO | 0154604 A1 | 8/2001 |
| WO | 02/07627 | 1/2002 |
| WO | 02/45589 A2 | 6/2002 |
| WO | 02/067798 | 9/2002 |
| WO | 02/080783 | 10/2002 |
| WO | 02/080784 | 10/2002 |
| WO | 02/080785 | 10/2002 |
| WO | 02/080786 | 10/2002 |
| WO | 02/080793 | 10/2002 |
| WO | 02/080794 | 10/2002 |
| WO | 02/080795 | 10/2002 |
| WO | 02/080796 | 10/2002 |
| WO | 02/080797 | 10/2002 |
| WO | 02/080798 | 10/2002 |
| WO | 02/080799 A1 | 10/2002 |
| WO | 02/081170 | 10/2002 |
| WO | 03/061500 | 7/2003 |
| WO | 03/101311 | 12/2003 |
| WO | 03/090630 A3 | 4/2004 |
| WO | 2004/032776 A1 | 4/2004 |
| WO | 2004/032777 A1 | 4/2004 |
| WO | 2004/052221 A1 | 6/2004 |
| WO | 2004/073488 A2 | 9/2004 |
| WO | 2004/073490 A2 | 9/2004 |
| WO | 2004/073753 A2 | 9/2004 |
| WO | 2004/082495 A1 | 9/2004 |
| WO | 2004/098383 A2 | 11/2004 |
| WO | 2004/103156 A2 | 12/2004 |
| WO | 2005/004734 A1 | 1/2005 |
| WO | 2005/004735 A1 | 1/2005 |
| WO | 2005/110264 A2 | 11/2005 |
| WO | 2006021269 A1 | 3/2006 |
| WO | 2008/045348 A2 | 4/2008 |
| WO | 2008/045350 A2 | 4/2008 |
| WO | 2008040483 A1 | 4/2008 |

OTHER PUBLICATIONS

Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.

(56) References Cited

OTHER PUBLICATIONS

Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 004491 dated Sep. 9, 2009.
Int'l Search Report EP 09 005051.9 dated Jul. 6, 2009.
Int'l Search Report EP 09 152267.2 dated Jun. 15, 2009.
Int'l Search Report EP 09 152898.4 dated Jun. 10, 2009.
Int'l Search Report EP 10 167655 dated Aug. 31, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Australian Examination Report dated Apr. 28, 2015 issued in Australian Appln. No. 2013206054.
U.S. Appl. No. 12/336,970, filed Dec. 17, 2008. Inventor: Sremcich et al.
Japanese Office Action dated May 23, 2013 issued in Japanese Appln. No. 2009077644.
European Search Report dated Feb. 23, 2017, issued in EP Appln. No. 13196880.
Australian Examination Report dated Mar. 1, 2017, issued in Australian Appln. No. 2016200297.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/ Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.

(56) References Cited

OTHER PUBLICATIONS

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

Int'l Search Report EP 98944778.4 dated Oct. 31, 2000.

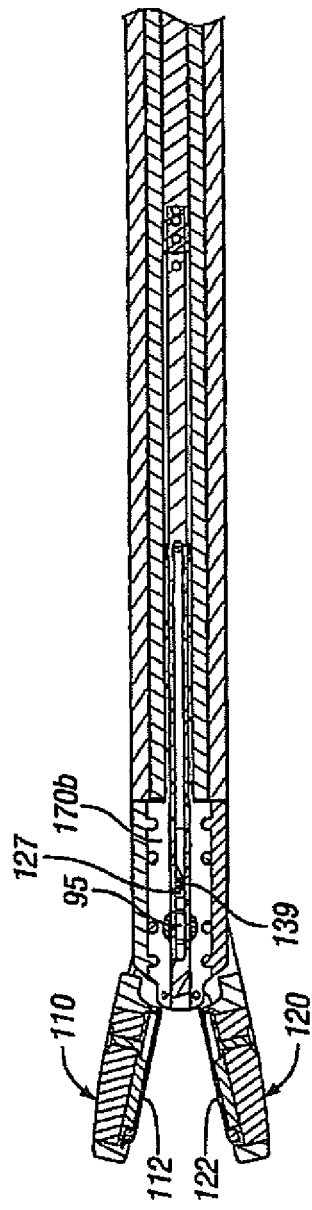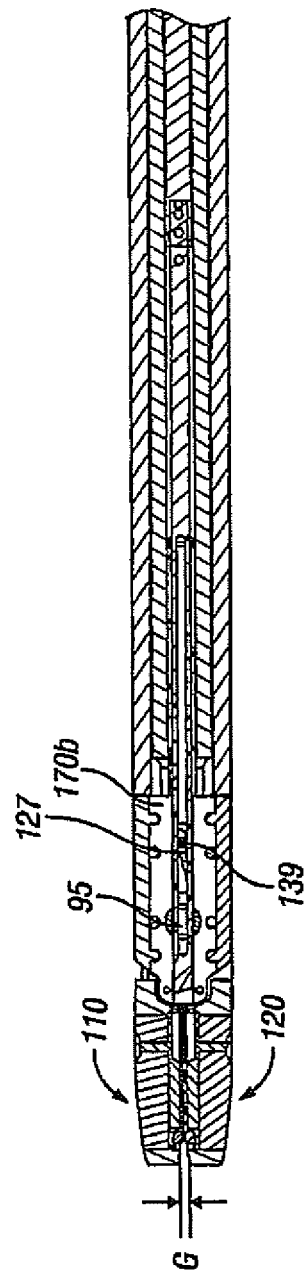

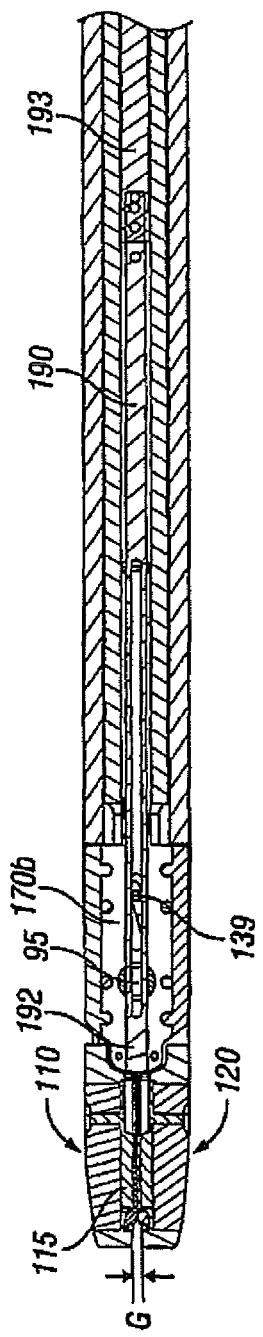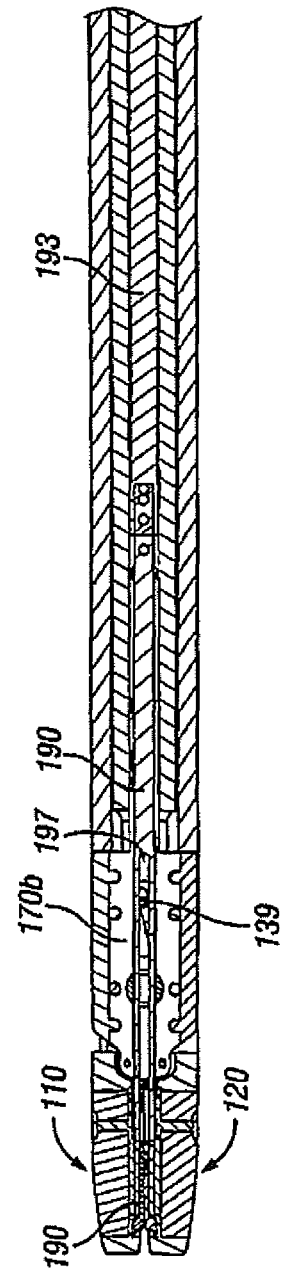
FIG. 10A
FIG. 10B

ENDOSCOPIC VESSEL SEALER AND DIVIDER FOR LARGE TISSUE STRUCTURES

CROSS REFERENCE TO RELATED APPLICATIONS

This application is a divisional of U.S. patent application Ser. No. 13/663,317, filed Oct. 29, 2012, now U.S. Pat. No. 9,113,903, which is a divisional of U.S. patent application Ser. No. 12/410,188, filed on Mar. 24, 2009, which claims the benefit of, and priority to, U.S. Provisional Patent Application Ser. No. 61/040,048, filed Mar. 27, 2008. U.S. patent application Ser. No. 12/410,188 is also a continuation-in-part of U.S. patent application Ser. No. 11/595,194, filed on Nov. 9, 2006, now U.S. Pat. No. 7,766,910, which claims the benefit of, and priority to, U.S. Provisional Patent Application Ser. No. 60/761,442, filed Jan. 24, 2006. The entire contents of each of these applications are hereby incorporated by reference herein.

BACKGROUND

The present disclosure relates to an electrosurgical forceps and more particularly, the present disclosure relates to an endoscopic bipolar electrosurgical forceps for sealing and/or cutting large tissue structures.

Technical Field

Electrosurgical forceps utilize both mechanical clamping action and electrical energy to affect hemostasis by heating the tissue and blood vessels to coagulate, cauterize and/or seal tissue. Many surgical procedures require cutting and/or ligating large blood vessels and large tissue structures. Due to the inherent spatial considerations of the surgical cavity, surgeons often have difficulty suturing vessels or performing other traditional methods of controlling bleeding, e.g., clamping and/or tying-off transected blood vessels or tissue. By utilizing an elongated electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, larger vessels can be more difficult to close using these standard techniques.

In order to resolve many of the known issues described above and other issues relevant to cauterization and coagulation, a recently developed technology has been developed by Valleylab, Inc. of Boulder, Colo., a division of Tyco Healthcare LP called vessel or tissue sealing. The process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass with limited demarcation between opposing tissue structures. Coagulation of small vessels is sufficient to permanently close them, while larger vessels and tissue need to be sealed to assure permanent closure.

In order to effectively seal larger vessels (or tissue) two predominant mechanical parameters are accurately controlled—the pressure applied to the vessel (tissue) and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal.

As mentioned above, in order to properly and effectively seal larger vessels or tissue, a greater closure force between opposing jaw members is required. It is known that a large closure force between the jaws typically requires a large moment about the pivot for each jaw. This presents a design challenge because the jaw members are typically affixed with pins which are positioned to have small moment arms with respect to the pivot of each jaw member. A large force, coupled with a small moment arm, is undesirable because the large forces may shear the pins. As a result, designers compensate for these large closure forces by either designing instruments with metal pins and/or by designing instruments which at least partially offload these closure forces to reduce the chances of mechanical failure. As can be appreciated, if metal pivot pins are employed, the metal pins should be insulated to avoid the pin acting as an alternate current path between the jaw members which may prove detrimental to effective sealing.

Increasing the closure forces between electrodes may have other undesirable effects, e.g., it may cause the opposing electrodes to come into close contact with one another which may result in a short circuit and a small closure force may cause pre-mature movement of the tissue during compression and prior to activation.

As a result thereof, providing an instrument which consistently provides the appropriate closure force between opposing electrode within a preferred pressure range will enhance the chances of a successful seal. As can be appreciated, relying on a surgeon to manually provide the appropriate closure force within the appropriate range on a consistent basis would be difficult and the resultant effectiveness and quality of the seal may vary. Moreover, the overall success of creating an effective tissue seal is greatly reliant upon the user's expertise, vision, dexterity, and experience in judging the appropriate closure force to uniformly, consistently and effectively seal the vessel. In other words, the success of the seal would greatly depend upon the ultimate skill of the surgeon rather than the efficiency of the instrument.

It has been found that the pressure range for assuring a consistent and effective seal for large vessels and tissue structures is between about 3 kg/cm$^2$ to about 16 kg/cm$^2$ and, desirably, within a working range of 7 kg/cm$^2$ to 13 kg/cm$^2$. As can be appreciated, manufacturing an instrument which is capable of consistently providing a closure pressure within these working ranges is quite a design challenge for instrument manufacturers.

Various force-actuating assemblies have been developed in the past for providing the appropriate closure forces to affect vessel sealing. For example, one such actuating assembly has been developed by Valleylab, Inc. of Boulder, Colo., a division of Tyco Healthcare LP, for use with Valleylab's vessel sealing and dividing instrument for sealing large vessels and tissue structures commonly sold under the trademark LIGASURE ATLAS®. The LIGASURE ATLAS® is presently designed to fit through a 10 mm cannula and includes a bi-lateral jaw closure mechanism and is activated by a foot switch. Co-pending U.S. application Ser. Nos. 10/179,863 and 10/116,944 and PCT Application Serial Nos. PCT/US01/01890 and PCT/7201/11340 describe in detail the operating features of the LIGASURE ATLAS® and various methods relating thereto. The contents of all of these applications are hereby incorporated by reference herein.

Other force-actuating assemblies have also been developed by the Valleylab, Inc. of Boulder, Colo., a division of Tyco Healthcare LP, for use with Valleylab's vessel sealing and dividing instrument for sealing large vessels and tissue structures commonly sold under the trademark LIGASURE 5 mm.™ The LIGASURE 5 mm™ is presently designed to fit through a 5 mm cannula and includes a unilateral jaw closure mechanism and is activated by a hand switch. Co-pending U.S. application Ser. Nos. 10/460,926 and 10/953,757 describe in detail the operating features of the LIGASURE 5 mm™ and various methods relating thereto. The contents of both of these applications are hereby incorporated by reference herein.

It would be desirous to develop a vessel sealing instrument which consistently produces the required mechanical forces necessary to close the jaw members about very large tissue structures within a preferred pressure range. It would also be desirous for the instrument to provide a mechanical advantage for manipulating the jaw members and clamping tissue, such that, for example, the jaw members can be closed on tissue, easier, quicker and with less user force than previously envisioned to clamp the tissue.

SUMMARY

The presently disclosed forceps includes a housing having a shaft affixed thereto. The shaft includes a longitudinal axis defined therethrough and a pair of jaw members disposed at a distal end thereof. The jaw members are adapted to connect to a source of electrosurgical energy such that the jaw members are capable of conducting energy through tissue held therebetween to affect a tissue seal. A drive assembly having a selectively advanceable drive sleeve is configured to move the jaw members relative to one another from a first position wherein the jaw members are disposed in spaced relation relative to one another to a second position wherein the jaw members are closer to one another for manipulating tissue.

The forceps also includes a movable handle which is rotatable about a pivot to force a drive flange of the drive assembly to move the jaw members between the first and second positions. The pivot is located a fixed distance above the longitudinal axis whereas the drive flange is located generally along the longitudinal axis. A selectively advanceable knife assembly is included having a knife bar which moves a knife to cut tissue between jaw members. A knife lockout mechanism operatively connects to the drive assembly. Movement of the drive assembly moves the lockout mechanism from a first orientation in obstructive relationship with the knife bar to prevent movement thereof to a second position which allows selective, unencumbered movement of the knife bar to cut tissue disposed between the jaw members.

In one embodiment, the drive assembly includes a drive stop disposed near the proximal end thereof. The drive stop is operatively engaged with the knife lockout mechanism such that selective movement of the drive assembly causes the drive stop to move or rotate the knife lockout mechanism between the first position and the second position.

In another embodiment, the knife bar includes a generally t-shaped proximal end dimensioned to operatively engage a corresponding slot defined within the housing. The slot configured to guide the movement of the knife bar during translation thereof. The knife lockout mechanism may be dimensioned to obstruct the t-shaped proximal end of the knife bar when disposed in the first position. The knife assembly may include a cuff at the distal end of the knife bar which is dimensioned to encapsulate and move atop the drive sleeve upon movement of the knife bar.

In yet another embodiment, the knife bar is operatively coupled to a knife slidingly disposed within the shaft and the forceps further includes a finger actuator operatively coupled to the knife assembly. Movement of the finger actuator moves the knife bar which, in turn, moves the knife to cut tissue disposed between the jaw members.

A finger actuator may be operatively connected to the knife assembly. The finger actuator includes two generally u-shaped flanges which rotate about a pivot to abut and force the cuff distally which, in turn, results in distal translation of the knife bar. A spring may also be included which biases the knife assembly in a proximal-most orientation. A spring may also be included which biases the knife lockout mechanism in the first position.

A hand switch may be disposed within the housing which is adapted to connect to the source of electrosurgical energy. The hand switch being configured to allow a user to selectively supply bipolar energy to the jaw members to effect a tissue seal. At least one of the jaw members may include one or a series of stop members disposed thereon for regulating the distance between the jaw members during the sealing process.

Another embodiment of the present disclosure includes a housing having a shaft affixed thereto. The shaft includes a longitudinal axis defined therethrough and a pair of jaw members disposed at a distal end thereof. The jaw members are adapted to connect to a source of electrosurgical energy such that the jaw members are capable of conducting energy through tissue held therebetween to affect a tissue seal. A drive assembly having a selectively advanceable drive sleeve is configured to move the jaw members relative to one another from a first position wherein the jaw members are disposed in spaced relation relative to one another to a second position wherein the jaw members are closer to one another for manipulating tissue.

A movable handle is included which is rotatable about a pivot to force a drive flange of the drive assembly to move the jaw members between the first and second positions. The pivot is located a fixed distance above the longitudinal axis and the drive flange is located generally along the longitudinal axis. A knife assembly is included which has a knife bar with a t-shaped proximal end. The knife assembly is selectively movable to advance the knife bar which, in turn, moves a knife to cut tissue between jaw members.

A knife lockout mechanism operatively connects to the drive assembly. Movement of the drive sleeve of the drive assembly pivots the knife lockout mechanism between a first orientation in obstructive relationship with the t-shaped proximal end of the knife bar to prevent movement thereof to a second position which allows selective, unencumbered movement of the t-shaped proximal end of the knife bar to reciprocate the knife to cut tissue disposed between the jaw members.

BRIEF DESCRIPTION OF THE DRAWINGS

Various embodiments of the subject instrument are described herein with reference to the drawings wherein:

FIG. 8B is an enlarged, side cross-sectional view showing the jaw members in a spaced apart orientation;

FIG. 8C is an enlarged, side cross-sectional view showing the jaw members in a closed orientation;

FIG. 10A is an enlarged, side cross-sectional view showing the end effector in a closed position and the knife in an unactuated position;

FIG. 10B is an enlarged, side cross-sectional view showing the end effector in a closed position and the knife in an actuated position;

DETAILED DESCRIPTION

Figure 1A:
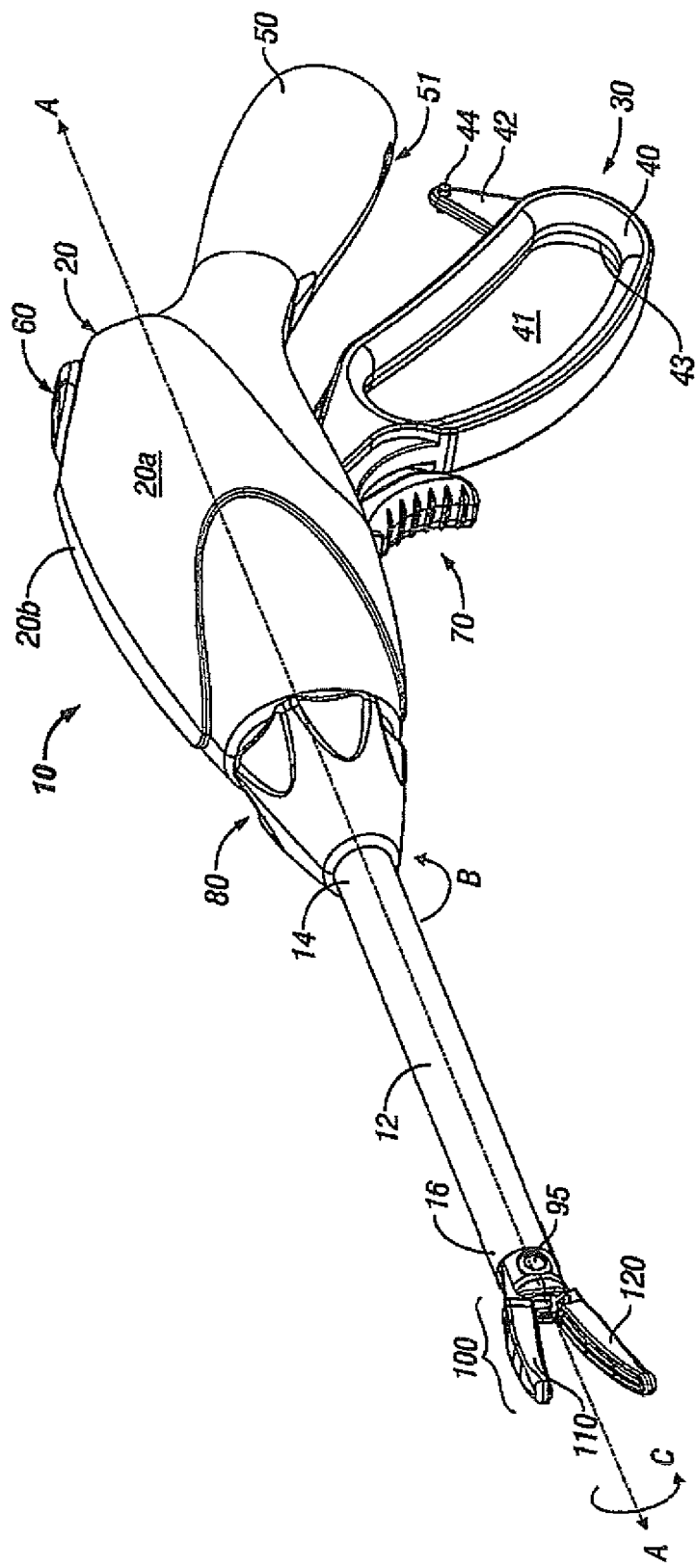
FIG. 1A is a perspective view of a bipolar forceps shown in open configuration and including a housing, a shaft, handle assembly, trigger assembly and an end effector assembly according to the present disclosure.
Figure 1B:
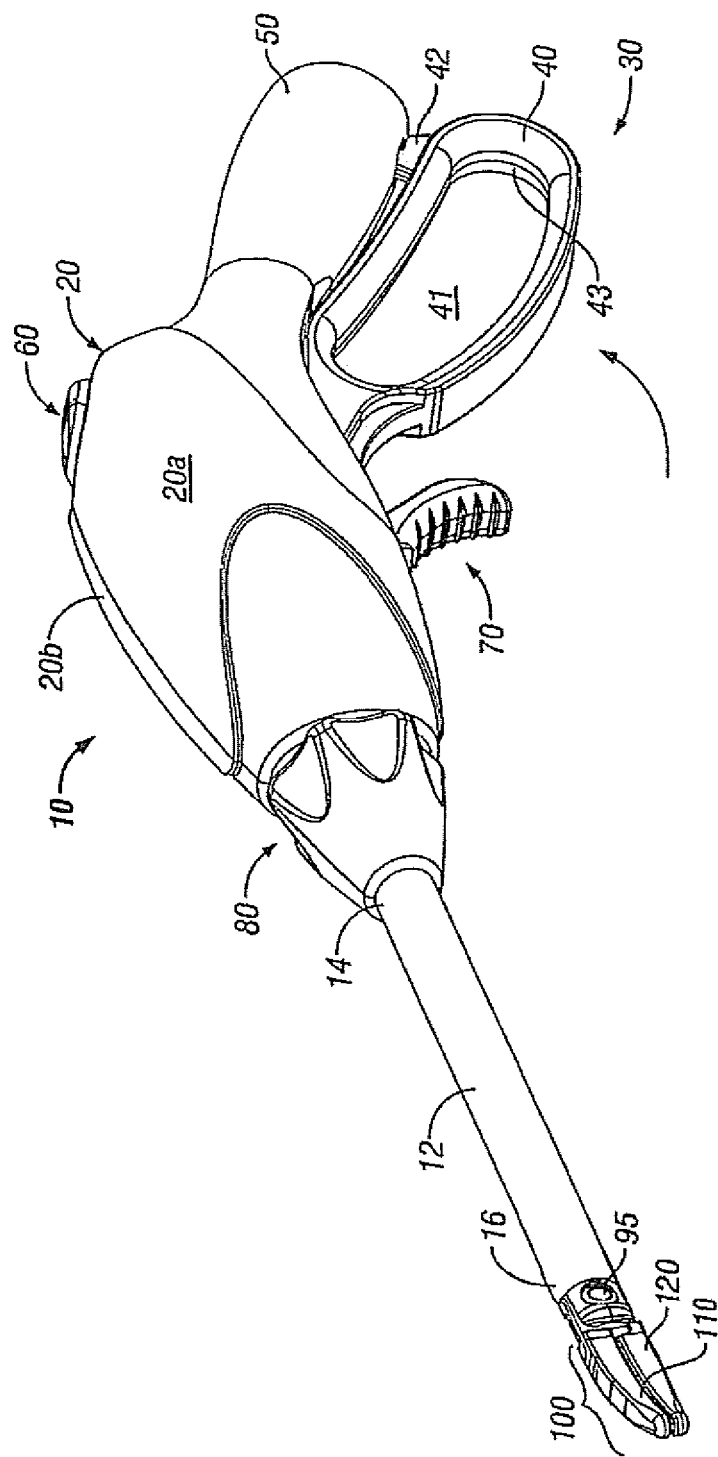
FIG. 1B is a perspective view of the bipolar forceps of FIG. 1A shown in closed configuration.
Figure 2:
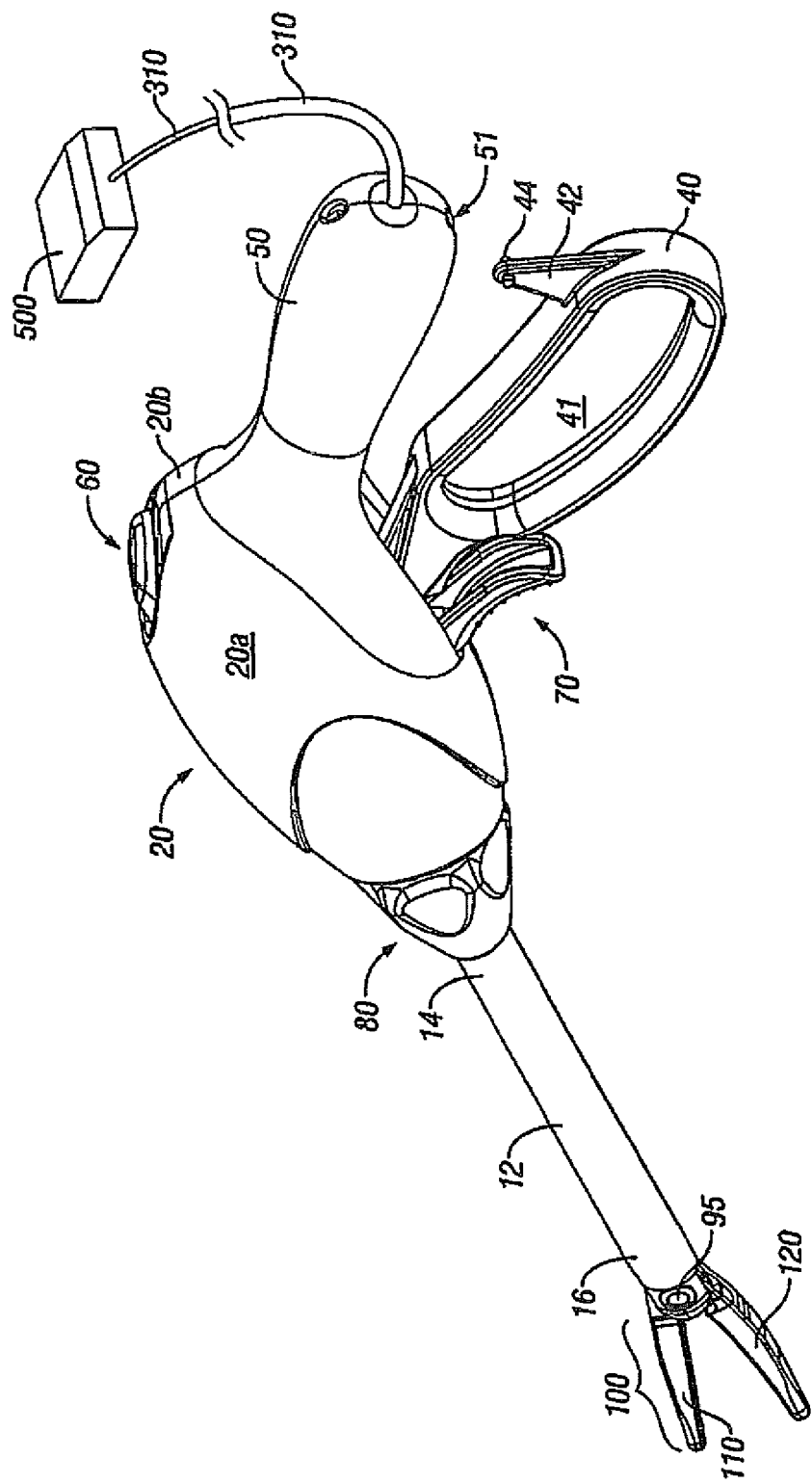
FIG. 2 is a rear view of the forceps of FIG. 1A.

Turning now to FIGS. 1A-2, one embodiment of a bipolar forceps 10 is shown for use with various surgical procedures and generally includes a housing 20, a handle assembly 30, a rotating assembly 80, a trigger assembly 70 and an end effector assembly 100 which mutually cooperate to grasp, seal and divide large tubular vessels and large vascular tissues. Although the majority of the figure drawings depict a bipolar forceps 10 for use in connection with endoscopic surgical procedures, the present disclosure may be used for more traditional open surgical procedures. For the purposes herein, the forceps 10 is described in terms of an endoscopic instrument, however, it is contemplated that an open version of the forceps may also include the same or similar operating components and features as described below.

Forceps 10 includes a shaft 12 which has a distal end 16 dimensioned to mechanically engage the end effector assembly 100 and a proximal end 14 which mechanically engages the housing 20. Details of how the shaft 12 connects to the end effector are described in more detail below with respect to FIGS. 13 and 14. The proximal end 14 of shaft 12 is received within the housing 20 and the connections relating thereto are also described in detail below with respect to FIGS. 11 and 12. In the drawings and in the descriptions which follow, the term "proximal," as is traditional, will refer to the end of the forceps 10 which is closer to the user, while the term "distal" will refer to the end which is farther from the user.

As best seen in FIGS. 1A and 2, forceps 10 also includes an electrosurgical cable 310 which connects the forceps 10 to a source of electrosurgical energy, e.g., a generator 500 (shown schematically). It is contemplated that generators such as those sold by Valleylab—a division of Tyco Healthcare LP, located in Boulder Colo. may be used as a source of electrosurgical energy, e.g., Ligasure™ Generator, FORCE EZ™ Electrosurgical Generator, FORCE FX™ Electrosurgical Generator, FORCE 1C™, FORCE 2™ Generator, SurgiStat™ II or other envisioned generators which may perform different or enhanced functions. One such system is described in commonly-owned U.S. Pat. No. 6,033,399 entitled "ELECTROSURGICAL GENERATOR WITH ADAPTIVE POWER CONTROL" the entire contents of which are hereby incorporated by reference herein. Other systems have been described in commonly-owned U.S. Pat. No. 6,187,003 entitled "BIPOLAR ELECTROSURGICAL INSTRUMENT FOR SEALING VESSELS" the entire contents of which are also incorporated by reference herein.

In one embodiment, the generator 500 includes various safety and performance features including isolated output, independent activation of accessories. It is envisioned that the electrosurgical generator includes Valleylab's Instant Response™ technology features which provides an advanced feedback system to sense changes in tissue 200 times per second and adjust voltage and current to maintain appropriate power. The Instant Response™ technology is believed to provide one or more of the following benefits to surgical procedure:

Consistent clinical effect through all tissue types;
Reduced thermal spread and risk of collateral tissue damage;
Less need to "turn up the generator"; and
Designed for the minimally invasive environment.

Cable 310 is internally divided into cable leads 310a, 310b and 325b which are designed to transmit electrical potentials through their respective feed paths through the forceps 10 to the end effector assembly 100. More particularly, cable feed 325b connects through the forceps housing 20 and through the rotating assembly to jaw member 120. Lead 310a connects to one side of the switch 60 and lead 310c connects to the opposite side of the switch 60 such that upon activation of the switch energy is transmitted from lead 310a to 310c. Lead 310c is spliced with lead 310b which connects through the rotating assembly to jaw member 110. Details relating to the electrical connections are explained in more detail below with the discussion of the switch 60.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Fixed handle 50 is oriented approximately 30 degrees relative a longitudinal axis "A-A defined through shaft 12. Fixed handle 50 may include one or more ergonomic enhancing elements to facilitate handling, e.g., scallops, protuberances, elastomeric material, etc.

Rotating assembly 80 is operatively associated with the housing 20 and is rotatable approximately 180 degrees about a longitudinal axis "A-A" (See FIG. 1A). Details of the rotating assembly 80 are described in more detail with respect to FIG. 11.

As mentioned above, end effector assembly 100 is attached at the distal end 14 of shaft 12 and includes a pair of opposing jaw members 110 and 120. Movable handle 40 of handle assembly 30 is ultimately connected to a drive assembly 130 which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

It is envisioned that the forceps 10 may be designed such that it is fully or partially disposable depending upon a particular purpose or to achieve a particular result. For example, end effector assembly 100 may be selectively and releasably engageable with the distal end 16 of the shaft 12 and/or the proximal end 14 of shaft 12 may be selectively and releasably engageable with the housing 20 and the handle assembly 30. In either of these two instances, the forceps 10 would be considered "partially disposable" or "reposable", i.e., a new or different end effector assembly 100 (or end effector assembly 100 and shaft 12) selectively replaces the old end effector assembly 100 as needed. As can be appreciated, the presently disclosed electrical connections would have to be altered to modify the instrument to a reposable forceps.

Turning now to the more detailed features of the present disclosure as described with respect to FIGS. 1A-14, movable handle 40 includes a finger loop 43 which has an aperture 41 defined therethrough which enables a user to grasp and move the handle 40 relative to the fixed handle 50. Finger loop 43 is typically ergonomically enhanced and may include one or more gripping elements (not shown) disposed along the inner peripheral edge of aperture 41 which are designed to facilitate gripping of the movable handle 40 during activation, e.g., a so called "soft touch" material. Gripping elements may include one or more protuberances, scallops and/or ribs to enhance gripping.

Figure 5A:
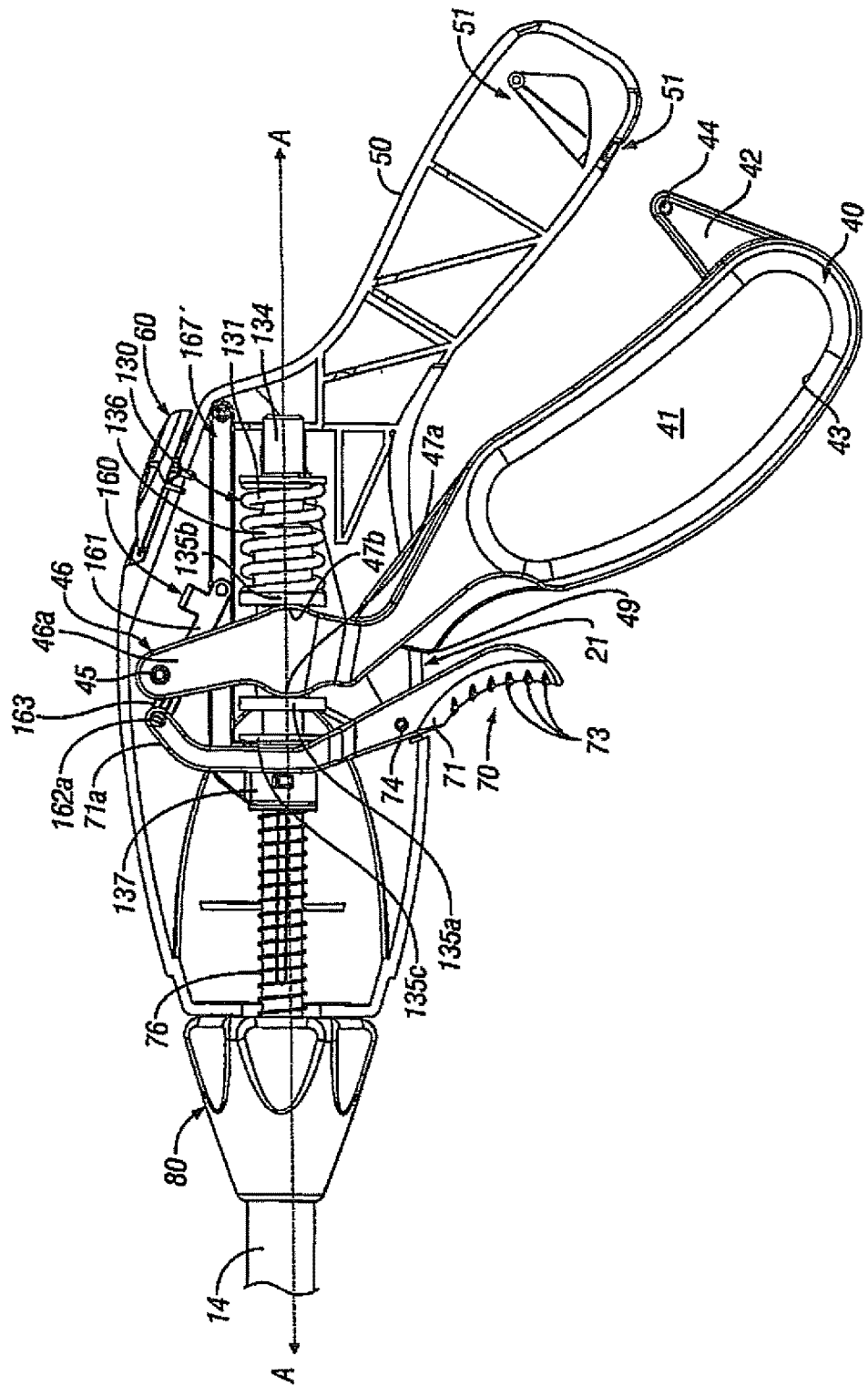
FIG. 5A is side view of the endoscopic forceps of FIG. 1A with the internal working components of the forceps exposed.
Figure 5B:
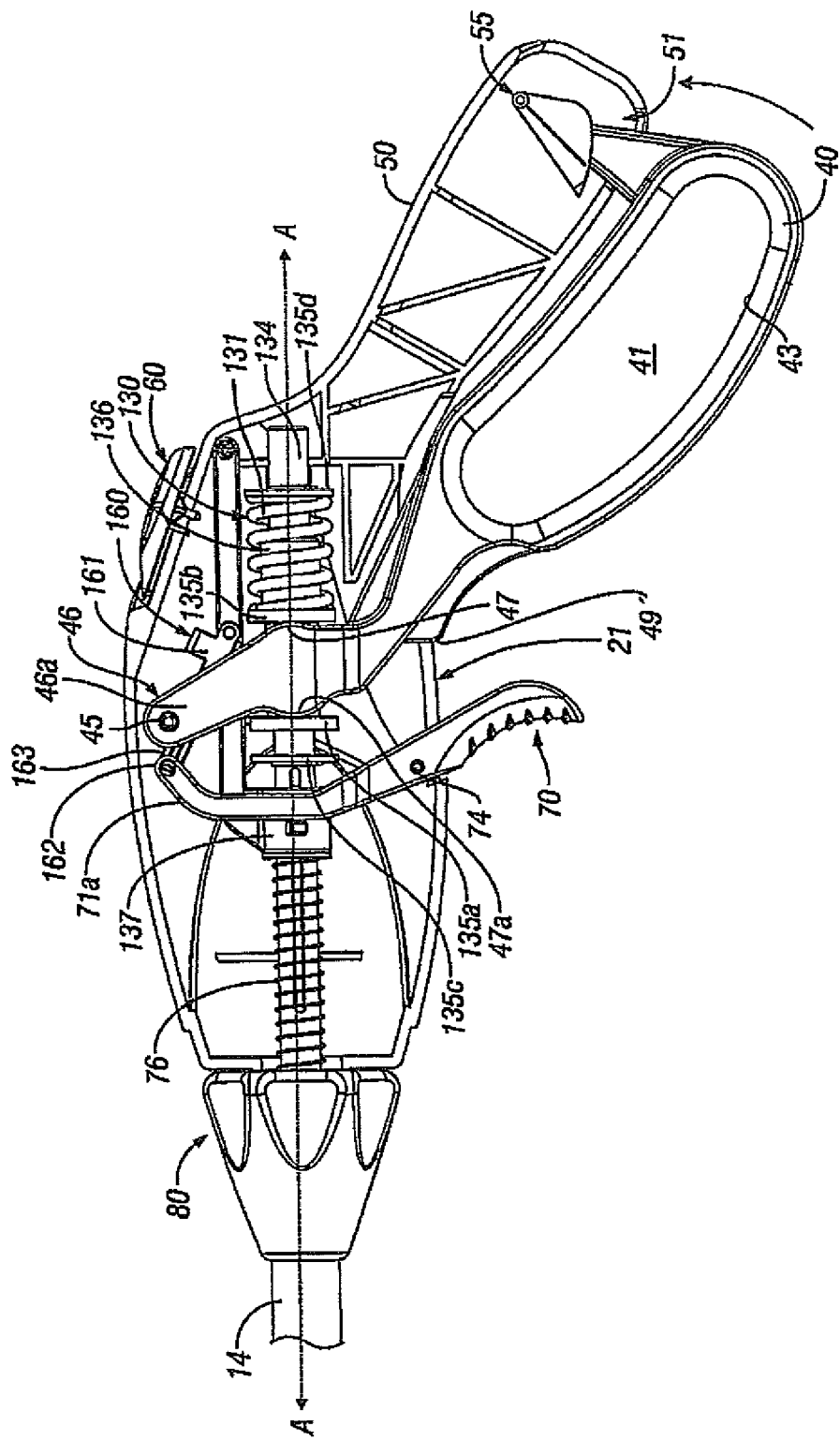
FIG. 5B is side view of the endoscopic forceps of FIG. 1B with the internal working components of the forceps exposed.

As best seen in FIGS. 5A and 5B, movable handle 40 is selectively movable about a pivot pin 45a from a first position relative to fixed handle 50 to a second position in closer proximity to the fixed handle 50 which, as explained below, imparts movement of the jaw members 110 and 120 relative to one another. The movable handle includes a clevis 46 which forms a pair of upper flanges 46a and 46b each having an aperture at an upper end thereof for receiving a pivot pin 45 (See FIG. 12) therethrough and mounting the upper end of the handle 40 to the housing 20. In turn, pivot pin 45 mounts to respective housing halves 20a and 20b. Pivot pin 45 is dimensioned to mount within socket 45a of housing half 20b.

Each upper flange 46a and 46b also includes a force-actuating flange or drive flange 47a and 47b (See FIG. 7), respectively, which are aligned along longitudinal axis "A" and which abut the drive assembly 130 such that pivotal movement of the handle 40 forces actuating flanges 47a and 47b against the drive assembly 130 which, in turn, closes the jaw members 110 and 120 (See FIGS. 5A and 5B). For the purposes herein, 47a and 47b which act simultaneously on the drive assembly 130 are referred to as "driving flange 47". A more detailed explanation of the inter-cooperating components of the handle assembly 30 and the drive assembly 130 is discussed below.

Figure 5C:
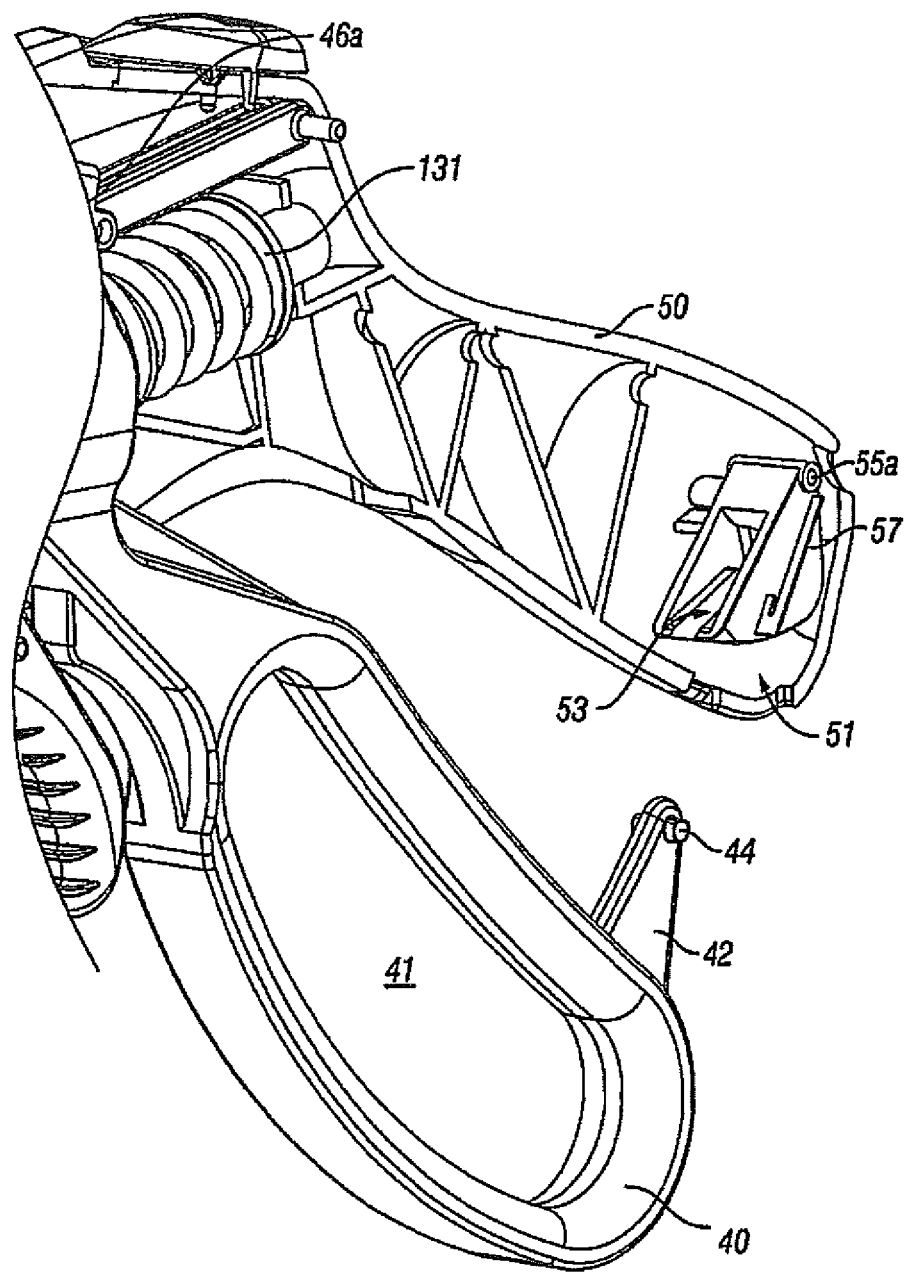
FIG. 5C is a greatly-enlarged, perspective view of the handle assembly in open configuration.

As best shown in FIG. 5C, the lower end of the movable handle 40 includes a flange 42 which is typically integrally associated with or operatively connected to movable handle 40. Flange 42 is typically T-shaped and includes a pin-like element 44 which projects laterally or transversally from a distal end thereof and is configured to engage a corresponding railway 55 disposed within fixed handle 50. More particularly, the pin 44 is configured to ride within a predefined channel 53 disposed within the railway 55 to lock the movable handle 40 relative to the fixed handle 50 upon reciprocation thereof. Additional features with respect to the t-shaped pin 44 are explained below in the detailed discussion of the operational features of the forceps 10.

Movable handle 40 is designed to provide a distinct mechanical advantage over conventional handle assemblies due to the unique position of the pivot pin 45 (i.e., pivot point) relative to the longitudinal axis "A" of the shaft 12 and the disposition of the driving flange 47 along longitudinal axis "A". In other words, it is envisioned that by positioning the pivot pin 45 above the driving flange 47, the user gains lever-like mechanical advantage to actuate the jaw members 110 and 120 enabling the user to close the jaw members 110 and 120 with lesser force while still generating the required forces necessary to effect a proper and effective tissue seal.

As shown best in FIGS. 3A-3F, 13 and 14, the end effector assembly 100 includes opposing jaw members 110 and 120 which cooperate to effectively grasp tissue for sealing purposes. The end effector assembly 100 is designed as a bilateral assembly, i.e., both jaw members 110 and 120 pivot relative to one another about a pivot pin 95 disposed therethrough. The jaw members 110 and 120 are curved to facilitate manipulation of tissue and to provide better "line of sight" for accessing organs and large tissue structures.

Figure 13:
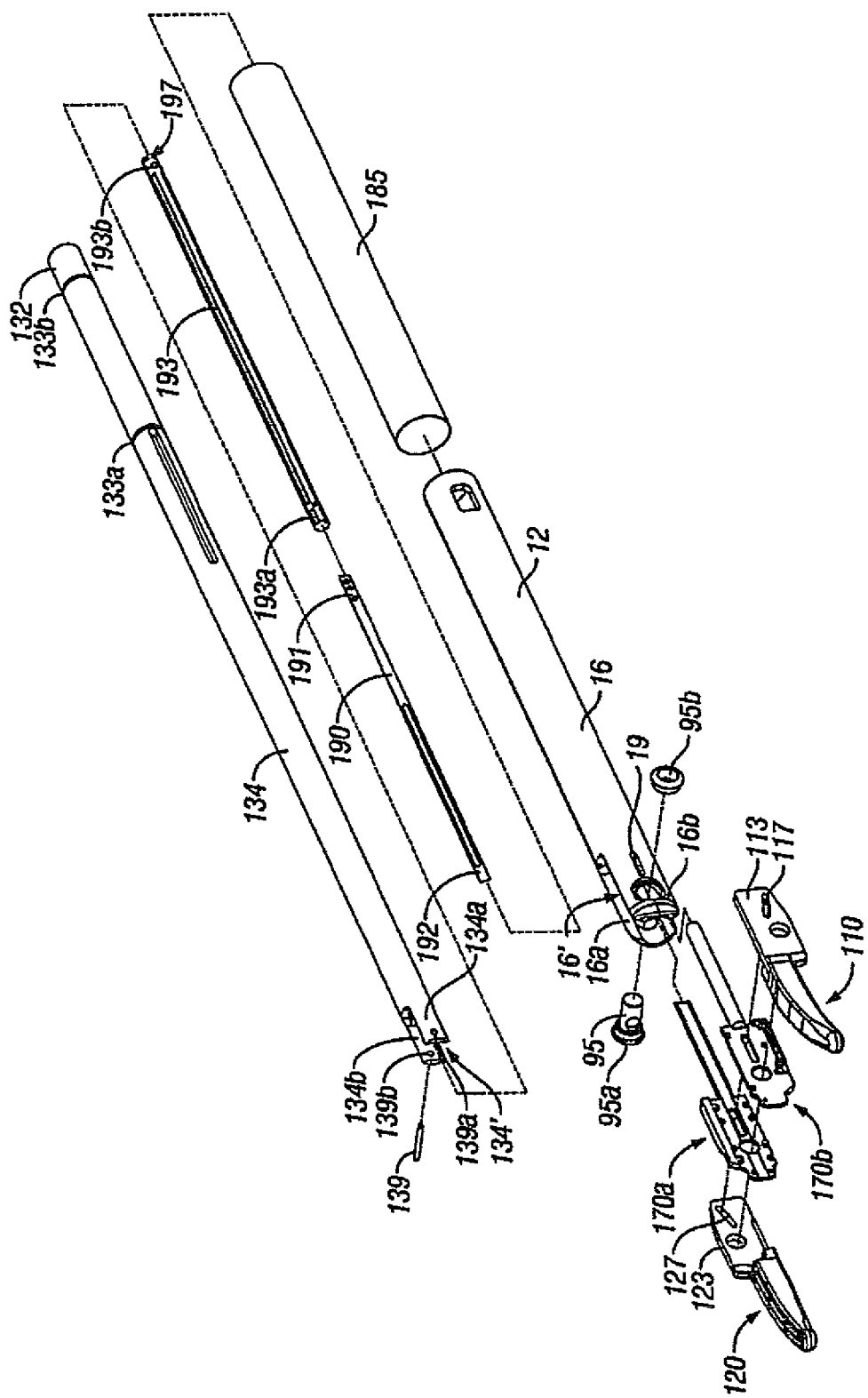
FIG. 13 is an enlarged, exploded perspective view of the end effector assembly and the shaft.
Figure 14:
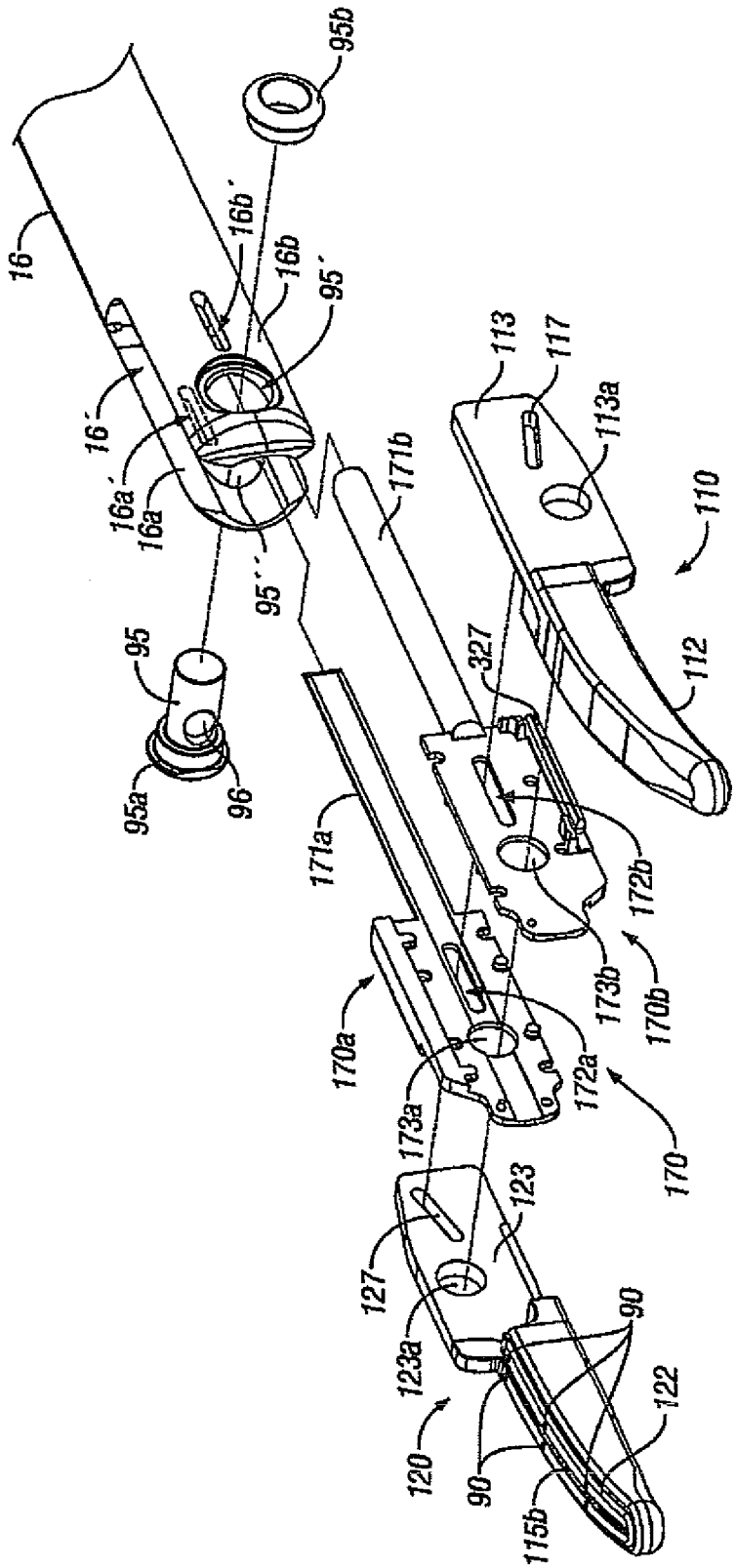
FIG. 14 is a greatly enlarged, exploded perspective view of the end effector assembly.

A reciprocating drive sleeve 134 is slidingly disposed within the shaft 12 and is remotely operable by the drive assembly 130 as explained in more detail below. Drive sleeve 134 includes a bifurcated distal end composed of halves 134a and 134b, respectively, which define a cavity 134' therebetween for receiving jaw members 110 and 120. More particularly and as best illustrated in FIGS. 13 and 14, jaw members 110 and 120 include proximal flanges 113 and 123, respectively, which each include an elongated angled slot 117 and 127, respectively, defined therethrough. A drive pin 139 (See FIG. 13) mounts jaw members 110 and 120 to the end of a sleeve 134 and within cavity 134' disposed between flanges 134a and 134b. Cam pin or drive pin 139 mounts through apertures 139a and 139b defined in flanges 134a and 134b, respectively, and is reciprocable within slots 16a' and 16b' disposed at the distal ends 16a and 16b of shaft 12 (See FIG. 14). It is envisioned that slots 16a' and 16b' may extend into aperture 95' and 95" to facilitate assembly of pin 139. Pin 139 may be composed of two mechanically interfacing elements which are dimensioned to frictionally receive one another to retain pin 139 in place once assembled. Alternatively or in addition, pin 139 may be held in place by one of several known manufacturing techniques including: laser or heat-based welding, press-fit mechanical interaction (or other mechanically interlocking geometry, adhesives, chemical bonding, etc. A component disposed on the outside of shaft 12 may also be utilized to retain the pin 139 in place once assembled. For example, a heat shrink material, adhesive tape, rubber or other insulating boot or silicone may be used for this purpose. It is also envisioned that a varying diameter version of pin 139 may be utilized to prevent the pin from coming loose once assembled. It is also envisioned that a cap or stem (not shown) arrangement may be employed for this purpose as well.

Drive sleeve 134, which ultimately connects to the drive assembly 130, is dimensioned to slidingly receive knife drive rod 193, knife 190 and posts 171a and 171b of halves 170a and 170b of knife guide 170. Drive sleeve 134, in turn, is received within shaft 12. Upon actuation of the drive assembly 130, the drive sleeve 134 reciprocates which, in turn, causes the drive pin 139 to ride within slots 117 and 127 to open and close the jaw members 110 and 120 as desired. The jaw members 110 and 120, in turn, pivot about pivot pin 95 disposed through respective pivot holes 113a and 123a disposed within flanges 113 and 123. As can be appreciated, squeezing handle 40 toward handle 50 pulls drive sleeve 134 and drive pin 139 proximally to close the jaw members 110 and 120 about tissue grasped therebetween and pushing the sleeve 134 distally opens the jaw members 110 and 120 for grasping purposes.

Turning back to the details of the jaw member 110 and 120 as best shown in FIGS. 3A-3F, jaw member 110 includes a support base 119 which extends distally from flange 113 and which is dimensioned to support an insulative plate 119' thereon. Insulative plate 119', in turn, is configured to support an electrically conductive tissue engaging surface or sealing plate 112 thereon. It is contemplated that the sealing plate 112 may be affixed atop the insulative plate 119' and support base 119 in any known manner in the art, snap-fit, overmolding, stamping, ultrasonically welded, etc. Support base 119 together with the insulative plate 119' and electrically conductive tissue engaging surface 112 are encapsulated by an outer insulative housing 116. Outer housing 116 includes a cavity 116a which is dimensioned to securely engage the electrically conductive sealing surface 112 as well as the support base 119 and insulative plate 119'. This may be accomplished by stamping, by overmolding, by overmolding a stamped electrically conductive sealing plate and/or by overmolding a metal injection molded seal plate or other more common methods known in the art (i.e., a conductive surface bound to a structural support via an insulating material). All of these manufacturing techniques produce jaw member 110 having an electrically conductive surface 112 which is substantially surrounded by an insulating housing or substrate 116.

Figure 3A:
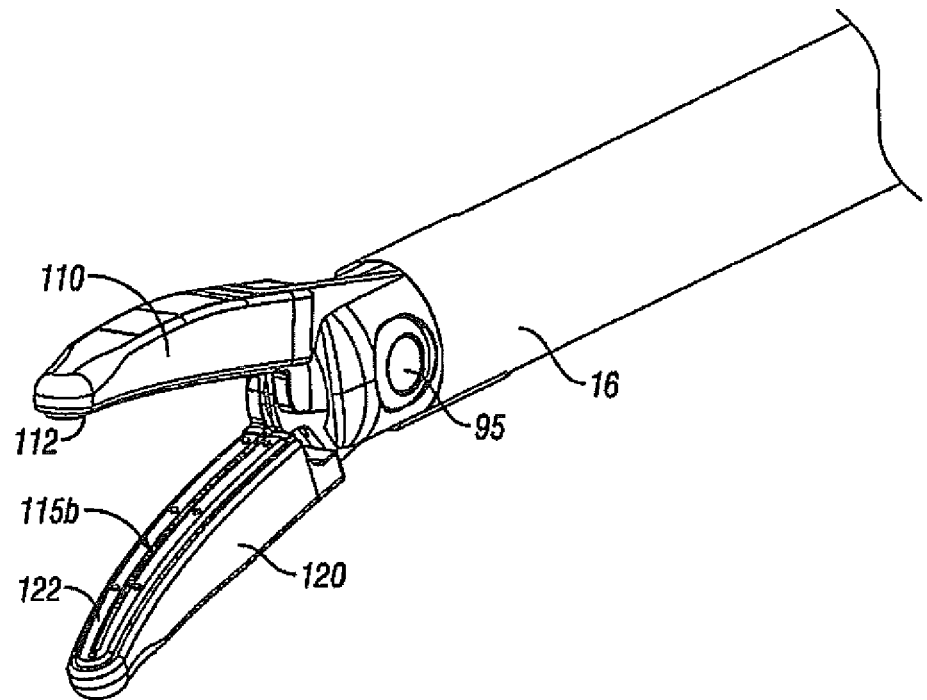
FIG. 3A is an enlarged, front perspective view of the end effector assembly of FIG. 1A shown in an open configuration.
Figure 3B:
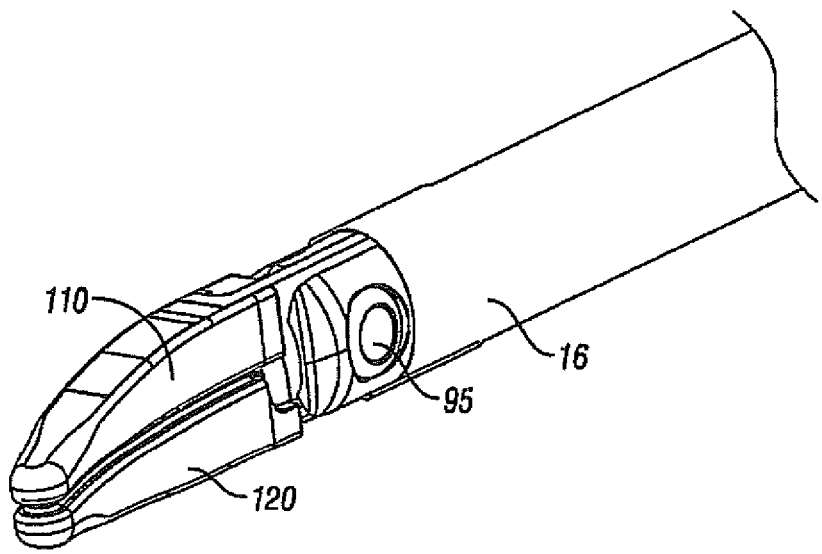
FIG. 3B is an enlarged, front perspective view of the end effector assembly of FIG. 1A shown in a closed configuration.
Figure 3C:
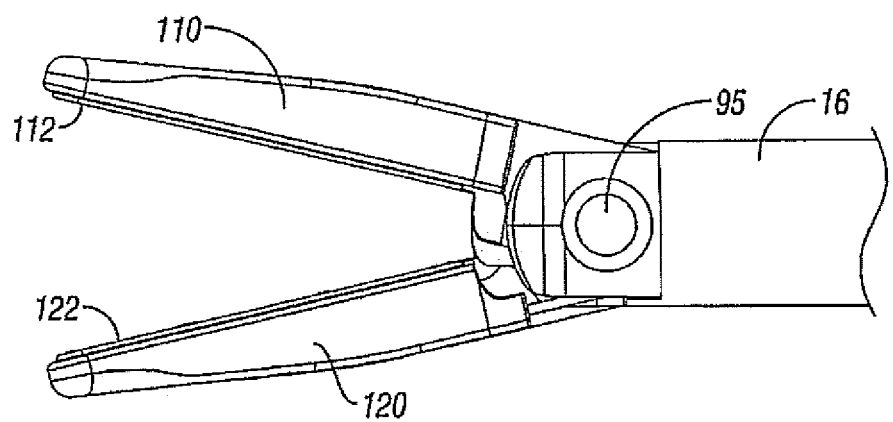
FIG. 3C is an enlarged, side view of the end effector assembly of FIG. 1A shown in open configuration.
Figure 3D:
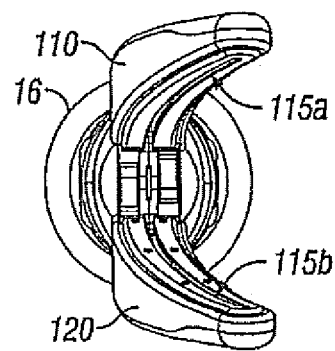
FIG. 3D is an enlarge, front view of the end effector assembly of FIG. 1A shown in open configuration.
Figure 3E:
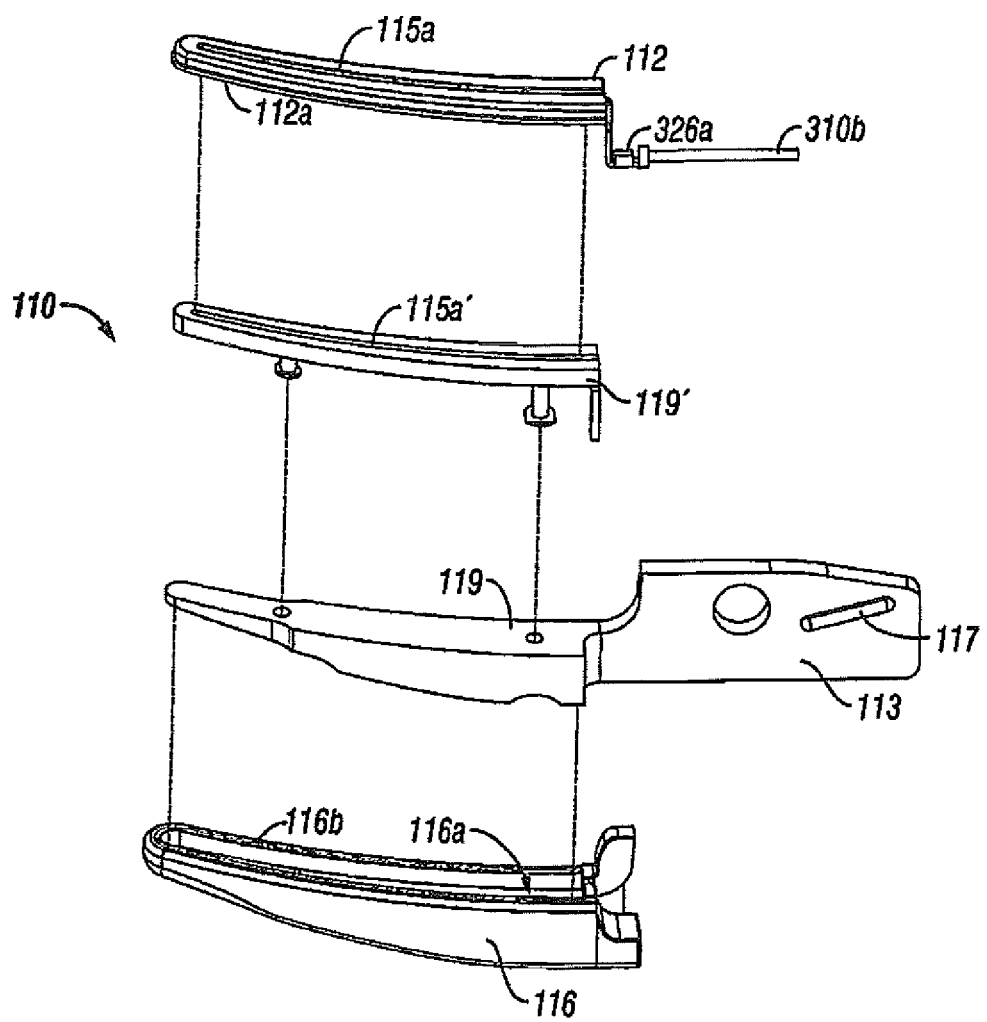
FIG. 3E is a greatly-enlarged, exploded perspective view of the top jaw member.

For example and as shown in FIG. 3E, the electrically conductive sealing plate 112 includes a peripheral flange 112a which surrounds the periphery of the sealing plate 112. Flange 112a is designed to matingly engage an inner lip 116b of the outer insulator 116. Again, this may be accomplished by any of the aforementioned known processes, e.g., overmolding. It is envisioned that lead 310b which extends from switch 60 terminates within the outer insulator 116 and is designed to electro-mechanically couple to the sealing plate 112 by virtue of a crimp-like connection 326a. Insulator 119', electrically conductive sealing surface 112 and the outer, non-conductive jaw housing 116 are preferably dimensioned to limit and/or reduce many of the known undesirable effects related to tissue sealing, e.g., flashover, thermal spread and stray current dissipation.

It is envisioned that the electrically conductive sealing surface 112 may also include an outer peripheral edge which has a pre-defined radius and the outer housing 116 meets the electrically conductive sealing surface 112 along an adjoining edge of the sealing surface 112 in a generally tangential position. At the interface, the electrically conductive surface 112 is raised relative to the outer housing 116. These and other envisioned embodiments are discussed in co-pending, commonly assigned Application Serial No. PCT/US01/11412 entitled "ELECTROSURGICAL INSTRUMENT WHICH REDUCES COLLATERAL DAMAGE TO ADJACENT TISSUE" by Johnson et al. and co-pending, commonly assigned Application Serial No. PCT/US01/11411 entitled "ELECTROSURGICAL INSTRUMENT WHICH IS DESIGNED TO REDUCE THE INCIDENCE OF FLASHOVER" by Johnson et al., the entire contents of both of which being hereby incorporated by reference herein.

The electrically conductive surface or sealing plate 112 and the outer housing 116, when assembled, form a longitudinally-oriented slot 115a defined therethrough for reciprocation of the knife blade 190 (See FIG. 13). It is envisioned that knife slot 115a cooperates with a corresponding knife slot 115b defined in jaw member 120 to facilitate longitudinal extension of the knife blade 190 along a preferred cutting plane to effectively and accurately separate the tissue along the formed tissue seal. Together, knife slots 115a and 115b form knife channel 115 for reciprocation of the knife 190. As best illustrated in FIGS. 3A-3F, knife channel 115 runs through the center of the jaw members 110 and 120, respectively, such that a blade 190 from the knife assembly 70 can cut the tissue grasped between the jaw members 110 and 120 when the jaw members 110 and 120 are in a closed position. As described in more detail below, handle 30a includes a passive lockout flange 49' which prevents actuation of the knife assembly 70 when the handle 40 is open thus preventing accidental or premature activation of the blade 190 through the tissue. In addition, the passive lockout flange 49' is dimensioned to force the trigger 70 to retract the knife 190 when the handle 40 is moved to an open position.

As explained above and as illustrated in FIGS. 3F, 8B, 8C, 10C and 10D, the knife channel 115 is formed when the jaw members 110 and 120 are closed. In other words, the knife channel 115 includes two knife channel halves—knife slot 115a disposed in sealing plate 112 of jaw member 110 and knife slot 115b disposed sealing plate 122 of jaw member 120. It is envisioned that the knife channel 115 may be dimensioned to include some degree of curvature to cause the knife 190 to move through tissue in a curved fashion. Alternatively, the knife channel 115 may be configured as a straight slot with no degree of curvature which, in turn, causes the knife 190 to move through the tissue in a substantially straight fashion. Insulating plate 119' also forms part of the knife channel 115 and includes slot 115a' defined therein which extends along insulating plate 119' and which aligns in vertical registration with knife slot 115a to facilitate translation of distal end 192 of the knife 190 therethrough.

As mentioned above, end effector assembly 100 also includes knife guide 170 which is dimensioned to facilitate alignment and translation of the knife 190 through and into the knife channel 115. More particularly, knife guide 170 includes half 170a and half 170b which mechanically interface to encapsulate the knife 190 upon assembly (See FIG. 13). It is envisioned that knife guide 170, once assembled, aligns the knife 190 for *facile* translation through knife channel 115 upon reciprocation of a knife drive rod 193 (FIG. 13). The operation of the drive rod 193 is described below with reference to the operational features of the forceps 10. Each half 170a and 170b of the knife guide 170 includes various interfaces thereon and apertures defined therein which allow unencumbered movement of the various operating features of the end effector assembly 100, e.g., pivot 95, drive pin 139 and knife 190. More particularly, halves 170a and 170b include apertures 173a and 173b, respectively, defined therethrough which allow passage of the pivot 95 during assembly. Halves 170a and 170b also include laterally-aligned slots 172a and 172b defined therein which allow reciprocation of the drive pin 139 upon opening and closing of the jaw members 110 and 120. One or more guides 327 (FIG. 14) may also be included to guide leads, e.g., lead 325a, along knife guide 170 and to the electrically conductive plates, e.g., plate 122. Knife guide halves 170a and 170b also include posts 171a and 171b which extend proximally into slot 16' upon assembly to engage knife 190.

Knife channel 115 runs through the center of the jaw members 110 and 120, respectively, such that a distal end 192 of the knife 190 can cut the tissue grasped between the jaw members 110 and 120 when the jaw members 110 and 120 are in a closed position. More particularly and as described in more detail below with respect to the operation of the forceps 10, the knife 190 can only be advanced through the tissue when the jaw members 110 and 120 are closed thus preventing accidental or premature activation of the knife 190 through the tissue. Passive lockout flange 49' detailed below prevents unintended translation of the knife 190 while the jaw members 110 and 120 are disposed in an open configuration. It is also envisioned that the knife 190 be dimensioned to allow other components to pass therethrough which additionally creates the benefit of enhancing he overall flexibility of the knife to facilitate passage through the knife channel 115.

Alternatively, one or both jaw members may also include a safety lockout to prevent the knife 190 from advancing while the jaw members are in an open configuration. Various safety lockout configurations are disclosed in commonly owned, co-pending U.S. application Ser. No. 10/962,116 entitled "OPEN VESSEL SEALING INSTRUMENT WITH CUTTING MECHANISM AND DISTAL LOCKOUT" and commonly owned, co-pending U.S. Provisional Application Ser. No. 60/722,177 entitled "IN-LINE VESSEL SEALER AND DIVIDER", the entire contents of which are both incorporated by reference herein.

Jaw member 120 includes similar elements to jaw member 110 such as jaw housing 126 which encapsulates a support plate 129, an insulator plate 129' and an electrically conductive sealing surface 122. Likewise, the electrically conductive surface 122 and the insulator plate 129', when assembled, include respective longitudinally-oriented knife slots 115b and 115b' defined therethrough for reciprocation of the knife blade 190. As mentioned above, when the jaw members 110 and 120 are closed about tissue, knife slots 115a and 115b form a complete knife channel 115 to allow longitudinal extension of the knife 190 in a distal fashion to sever tissue along a tissue seal. It is also envisioned that the knife channel 115 may be completely disposed in one of the two jaw members, e.g., jaw member 120, depending upon a particular purpose. It is also envisioned that jaw member 120 may be assembled in a similar manner as described above with respect to jaw member 110. More particularly, the sealing plate 122 may be dimensioned to include an outer peripheral rim 122a which is dimensioned to mechanically interface with an inner lip 126b of housing 126 to secure the sealing plate 122 to the housing 126 with plates 129 and 129' encapsulated therein.

Figure 3F:
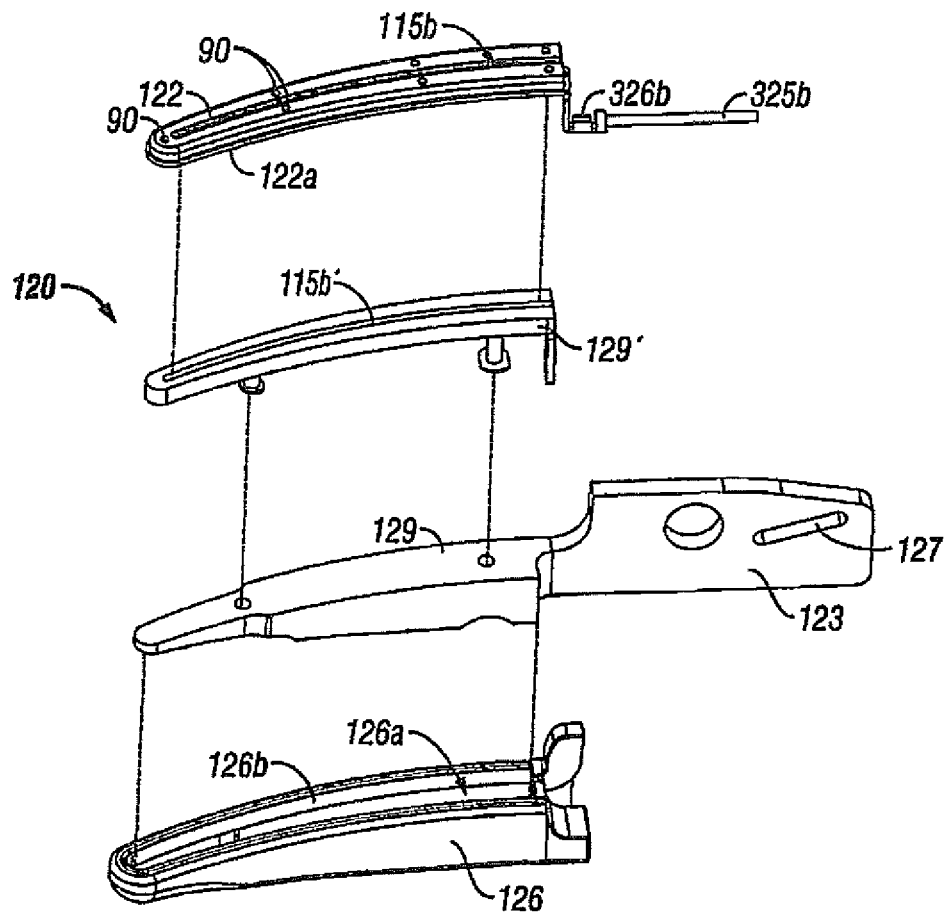
FIG. 3F is a greatly-enlarged, exploded perspective view of the bottom jaw member.
Figure 4:
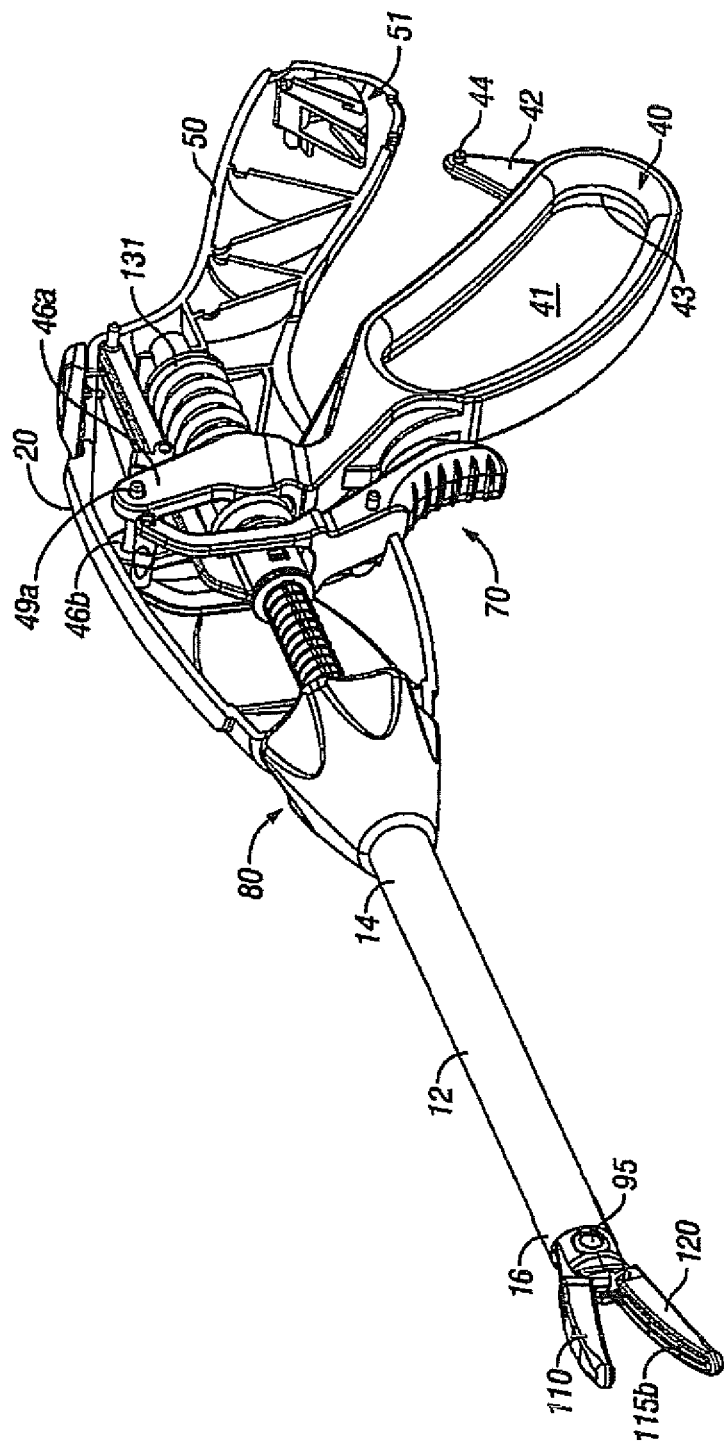
FIG. 4 is a perspective view of the endoscopic forceps of FIG. 1A with the internal working components of the forceps exposed.

As best seen in FIG. 3F, jaw member 120 includes a series of stop members 90 disposed on the inner facing surface of the electrically conductive sealing surface 122 to facilitate gripping and manipulation of tissue and to define a gap "G" (FIG. 10B) between opposing jaw members 110 and 120 during sealing and cutting of tissue. It is envisioned that the series of stop members 90 may be employed on one or both jaw members 110 and 120 depending upon a particular purpose or to achieve a desired result. A detailed discussion of these and other envisioned stop members 90 as well as various manufacturing and assembling processes for attaching and/or affixing the stop members 90 to the electrically conductive sealing surfaces 112, 122 are described in commonly-assigned, co-pending U.S. Application Serial No. PCT/US01/11413 entitled "VESSEL SEALER AND DIVIDER WITH NON-CONDUCTIVE STOP MEMBERS" by Dycus et al. which is hereby incorporated by reference in its entirety herein.

Jaw member 120 is connected to a second electrical lead 325b extending from switch 60 (See FIG. 6B) which terminates within the jaw housing 126 and is designed to electromechanically couple to the sealing plate 122 by virtue of a crimp-like connection 326b. As explained in more detail below, leads 310b and 325b allow a user to selectively supply bipolar electrosurgical energy to the jaw members 110 and 120 as needed during surgery.

Jaw members 110 and 120 are electrically isolated from one another such that electrosurgical energy can be effectively transferred through the tissue to form a tissue seal. For example and as best illustrated in FIGS. 3A-3F, each jaw member 110 and 120 includes a uniquely-designed electrosurgical cable path which transmits electrosurgical energy through the cable leads 310b and 325b to the electrically conductive sealing surfaces 112 and 122, respectively. Cable leads 310b and 325b are held loosely but securely along the cable path to permit rotation of the jaw members 110 and 120. As can be appreciated, this isolates electrically conductive sealing surfaces 112 and 122 from the remaining operative components of the end effector assembly 100 and shaft 12. The two electrical potentials are isolated from one another by virtue of the insulative sheathing surrounding the cable leads 310b and 325b.

Jaw members 110 and 120 are engaged to the end of rotating shaft 12 by pivot pin 95 such that rotation of the rotating assembly 80 correspondingly rotates shaft 12 (along with sleeve 134 and knife 190) which, in turn, rotates end effector assembly 100 (See FIG. 1A). More particularly, the distal end of rotating shaft 12 is bifurcated to include ends 16a and 16b which define a channel 16' therein for receiving jaw members 110 and 120. Pivot pin 95 includes a stem 95a and cap 95b arrangement which is dimensioned to engage through aperture 95' and 95" disposed in ends 16b and 16a, respectively. Upon assembly and as best illustrated in FIGS. 13 and 14, the stem 95a of pivot pin 95 extends, in order, through end 16a of shaft 12, aperture 123a of jaw member 120, aperture 173a of half 170a or knife guide 170, aperture 173b of half 170b of knife guide 170, aperture 113a of jaw member 110 and end 16b of shaft 12 to engage cap 95b. Slots 16a' and 16b' are defined within distal ends 16a and 16b and are dimensioned to allow reciprocation of drive pin 139 therein. Stem 95a includes a pass through hole 96 defined therein which allows passage of the knife 190 therethrough for severing tissue while still allowing a large rotational surface area for the jaw members during loading.

Figure 11:
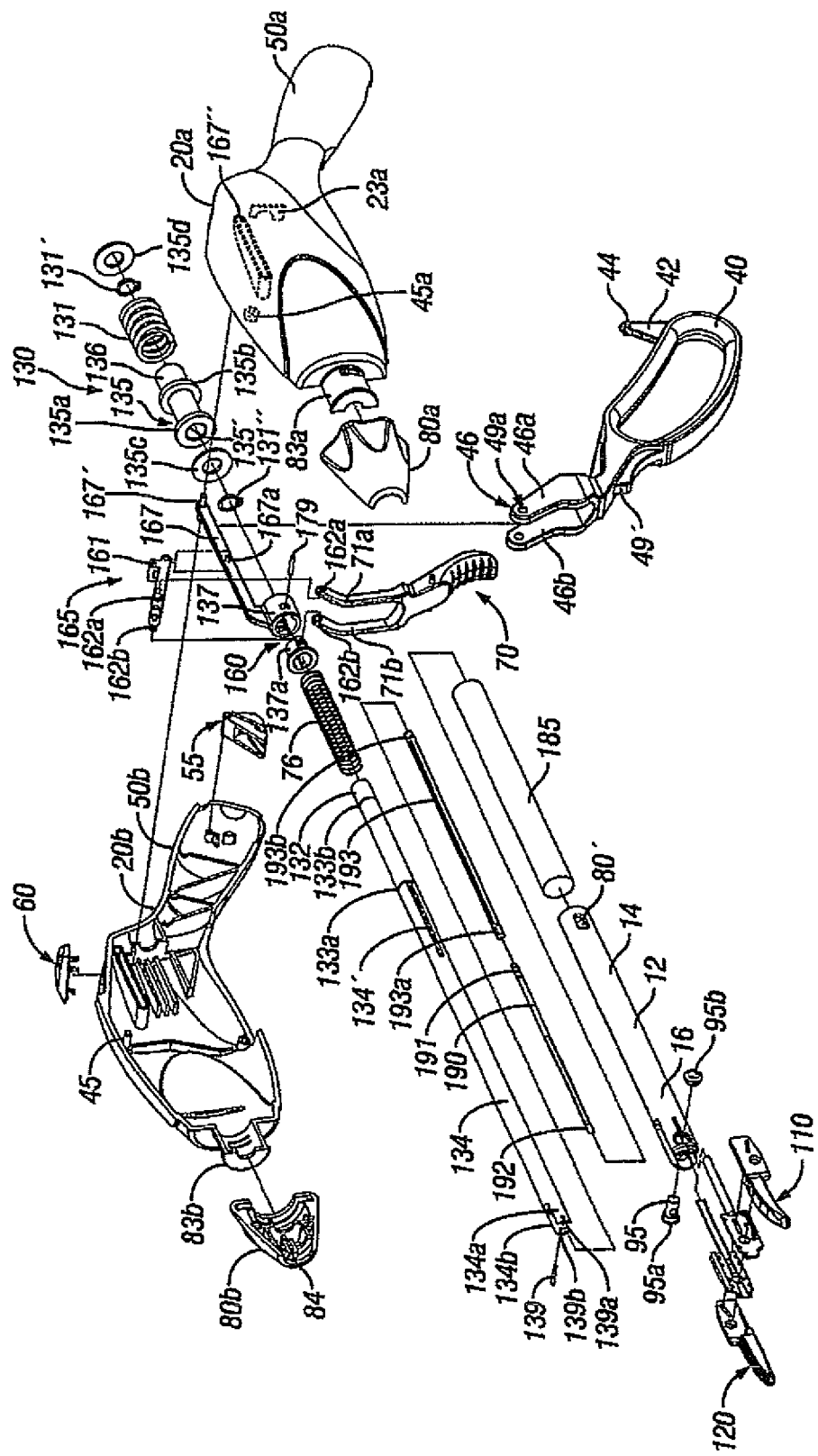
FIG. 11 is an exploded, perspective view of the forceps of FIG. 1A.
Figure 12:
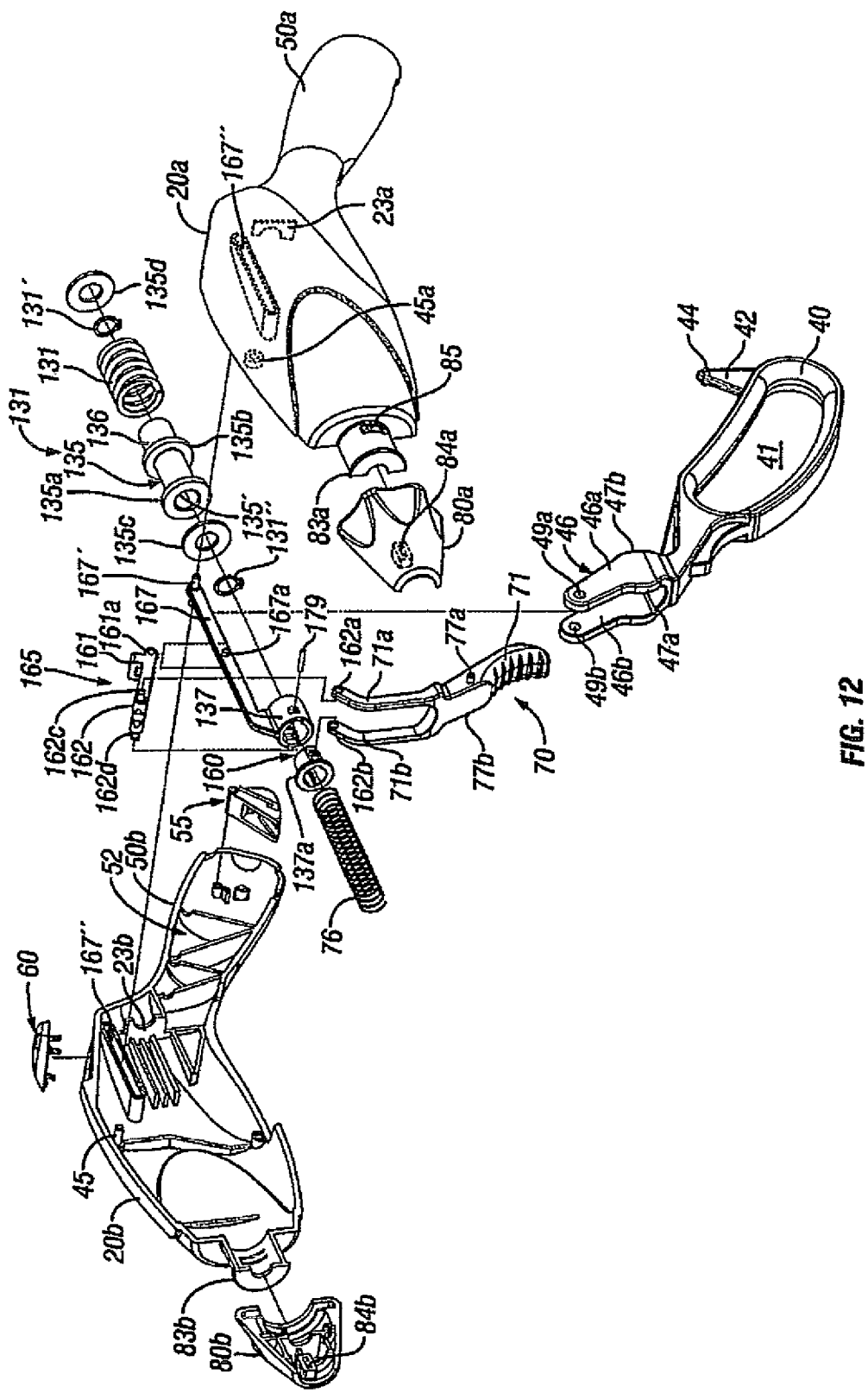
FIG. 12 is an enlarged, exploded perspective view of the housing.

Turning now to the cooperating components of the housing, FIGS. 5A, 5B, 6A, 6B, 11 and 12 show the details of the housing 20 and the component features thereof, namely, the drive assembly 130, the rotating assembly 80, the knife actuating assembly 160, the trigger assembly 70 and the handles 40 and 50. More particularly, FIGS. 5A and 5B show the above-identified assemblies and components in an assembled form in the housing 20 and FIGS. 11 and 12 show an exploded view of each of the above-identified assemblies and components.

As mentioned above and as best shown in FIGS. 11 and 12, the proximal end of shaft 12 is mechanically engaged to the housing 20. Housing 20 is formed from two (2) housing halves 20a and 20b which each include a plurality of interfaces which are dimensioned to mechanically align and engage one another to form housing 20 and enclose the internal working components of forceps 10. As can be appreciated, fixed handle 50 which, as mentioned above, is integrally associated with housing 20, includes halves 50a and 50b which take the shape of handle 50 upon the assembly of the housing halves 20a and 20b.

It is envisioned that a plurality of additional interfaces (not shown) may disposed at various points around the periphery of housing halves 20a and 20b for ultrasonic welding purposes, e.g., energy direction/deflection points. It is contemplated that ultrasonic welding provides better dimensional stability, strength and joint reliability that other, more traditional, methods. For example, the housing halves may be ultrasonically welded utilizing a combination of a primary weld joint using traditional triangular (or similar) energy directors to form a bonded joint coupled with a secondary hard stop surface (removed from the primary joint surface) for preventing over compression of the joint. A tertiary set of alignment pins may be utilized throughout the housing halves 20a and 20b which are configured to both accurately align the halves 20a and 20b during assembly and provide strength and stability during manufacture, handling and transport.

It is also contemplated that housing halves 20a and 20b (as well as the other components described below) may be assembled together in any fashion known in the art. For example, alignment pins, snap-like interfaces, tongue and groove interfaces, locking tabs, adhesive ports, etc. may all be utilized either alone or in combination for assembly purposes.

As best seen in FIGS. 11 and 12, rotating assembly 80 includes two C-shaped halves 80a and 80b which, when assembled, form the rotating assembly 80 which, in turn, house the drive assembly 130 and the knife actuating assembly 160. Half 80a includes a series of detents/flanges (not shown) which are dimensioned to engage a pair of corresponding sockets or other mechanical interfaces (not shown) disposed within rotating half 80b.

Half 80a also includes a tab 84a (phantomly illustrated) which together with a corresponding tab 84b disposed on half 80b cooperate to matingly engage slot 80' disposed on shaft 12. As can be appreciated, this permits selective rotation of the shaft 12 about axis "A-A" by manipulating the rotating member 80 in the direction of the arrow "B", which, in turn, rotates the end effector assembly in the direction of arrow "C" (See FIG. 1A). The rotating assembly may include one or more mechanical interfaces which essentially lock the rotating assembly in a fully counterclockwise rotational position or a fully clockwise rotational position. It is envisioned that this will allow left-handed or right-handed orientations for the end effector assembly for particular users.

As mentioned above and as best illustrated in FIGS. 5A, 5B, 6A and 6B, the movable handle 40 includes clevis 46 which forms upper flanges 46a and 46b which pivot about pins 45a and 45b to pull the reciprocating sleeve 134 along longitudinal axis "A-A" and force driving flanges 47a and 47b against the drive assembly 130 which, in turn, closes the jaw members 110 and 120. The various moving relationships of the flanges 47a and 47b and the drive assembly 130 are explained in more detail below with respect to the operation of the forceps 10. The arrangement of the driving flanges 47a and 47b and the pivot point 45 of the movable handle 40 provides a distinct mechanical advantage over conventional handle assemblies due to the unique position of the pivot pins 45a and 45b (i.e., pivot point) relative to the longitudinal axis "A-A" of the driving flanges 47a and 47b. In other words, by positioning the pivot pins 29a and 29b above the driving flanges 47a and 47b, the user gains lever-like mechanical advantage to actuate the jaw members 110 and 120. This reduces the overall amount of mechanical force necessary to close the jaw members 110 and 120 to affect a tissue seal. A similar mechanical arrangement is disclosed in commonly-owned U.S. patent application Ser. No. 10/460,926 the entire contents of which are incorporated by reference herein.

Handle 40 also includes a finger loop 43 which defines opening 41 which is dimensioned to facilitate grasping the handle 40. In one embodiment, finger loop 43 includes a rubber insert which enhances the overall ergonomic "feel" of the handle member 40. A locking flange 49' is disposed on the outer periphery of the handle member 40 above the finger loop 43. Locking flange 49' may be designed as a safety lock out mechanism to prevent the trigger assembly 70 from firing when the handle member 40 is oriented in a non-actuated position, i.e., the jaw members 110 and 120 are open. As can be appreciated, this would prevent accidental or premature severing of tissue prior to completion of the tissue seal.

Fixed handle 50 includes halves 50a and 50b which, when assembled, form handle 50. Fixed handle 50 includes a channel 51 defined therein which is dimensioned to receive flange 42 in a proximal moving manner when movable handle 40 is actuated. The t-shaped pin 44 of handle 40 is dimensioned for *facile* reception within channel 51 of handle 50. It is envisioned that flange 42 may be dimensioned to allow a user to selectively, progressively and/or incrementally move jaw members 110 and 120 relative to one another from the open to closed positions. For example, it is also contemplated that flange 42 may include a ratchet-like interface which lockingly engages the movable handle 40 and, therefore, jaw members 110 and 120 at selective, incremental positions relative to one another depending upon a particular purpose. Other mechanisms may also be employed to control and/or limit the movement of handle 40 relative to handle 50 (and jaw members 110 and 120) such as, e.g., hydraulic, semi-hydraulic, linear actuator(s), gas-assisted mechanisms and/or gearing systems.

Figure 5D:
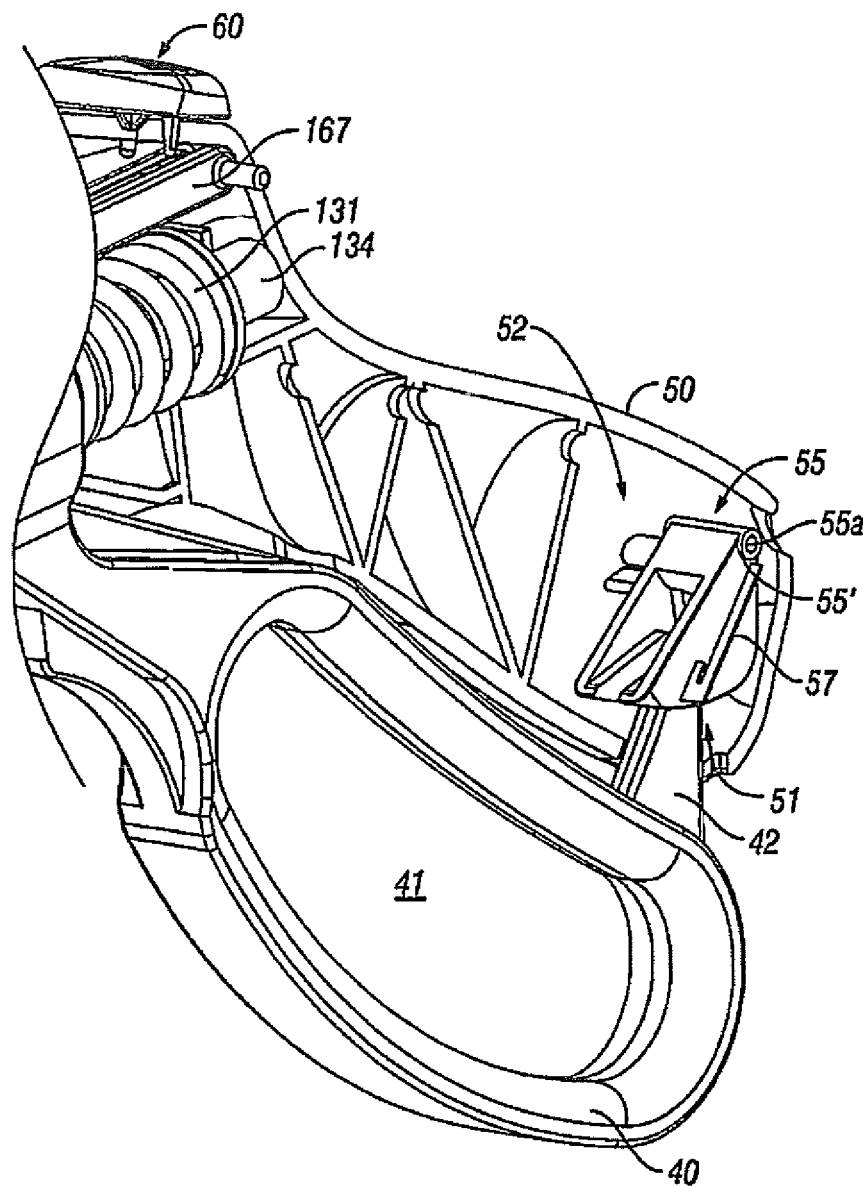
FIG. 5D is a greatly-enlarged, perspective view of the handle assembly in closed configuration.

As best illustrated in FIGS. 5D and 12, housing halves 20a and 20b when assembled form an internal cavity 52 which predefines the channel 51 within fixed handle 50 adjacent the railway 55 which reciprocates t-shaped pin 44 therein. Once assembled, the railway 55 is seated within cavity 52 in registration with entrance pathway 51 for reciprocation of the flange 42. Flange 42 and the housing halves 20a and 20b are designed to facilitate accurate and consistent reception of the t-shaped pin 44 into railway 55.

During movement of the flange 42 along the entrance to channel 51, the t-shaped pin 44 rides through passage 53 along railway 55 and is forced into a catch basin or seat 55' to lock the handle 40 relative to handle 50. When the user releases the handle 40, the catch basin 55' retains the t-shaped pin 44 in a secured position relative to the handle 50 as explained in further detail below. Railway 55 may be seated on one or pivot elements 55a which allows the railway 55 to pivot upon reception of the t-shaped pin 44 therethrough. A spring element 57 biases the railway 55 to return to the original reception position once the t-shaped pin 44 is seated. The railway 55, gain, may pivot in response to release of the t-shaped pin 44 from catch basin 55'. It is envisioned that actuation of the handle 40 along with the inter-cooperating elements of the drive assembly 130 close the jaw members 110 and 120 about tissue with a pre-determinable and consistent closure pressure to affect a tissue seal. As mentioned above, closure pressures for sealing large tissue structures preferably fall within the range of about 3 kg/cm$^2$ to about 16 kg/cm$^2$.

When handle 40 is regrasped, the t-shaped pin 44 is forced out of or disengaged from the catch basin 55' and moves along an exit pathway to release handle 40 from channel 51. A spring or other biasing member 57 may be employed to facilitate securing the flange 42 within the catch basin 55' and also configured to facilitate release of the flange 42 from catch basin 55' upon re-grasping of the handle 40.

As explained in more detail below, once actuated, handle 40 moves in a generally arcuate fashion towards fixed handle 50 about pivot pins 45a and 45b which forces driving assembly 130 proximally which, in turn, pulls reciprocating sleeve 134 in a generally proximal direction to close jaw members 110 and 120 relative to one another.

As best shown in FIGS. 5A, 5B and 11, the drive assembly 130 mounts atop the proximal portion of the drive sleeve 134. A pair of retaining rings or clips 131' and 131" (See FIG. 11) cooperate with a corresponding pair of relieved portions 133a and 133b disposed on the drive sleeve 134 to mount the drive assembly 130 atop the drive sleeve 134 such that relative movement of the drive assembly correspondingly moves the drive sleeve 134. As handle 40 pivots about pivot point 45 and moves relative to handle 50 and flange 42 is incorporated into channel 51 of fixed handle 50, the driving flanges 47a and 47b, through the mechanical advantage of the above-the-center pivot point, force the drive assembly 130 proximally against spring 131.

As a result thereof, drive sleeve 134 reciprocates proximally which, in turn, closes the jaw members 110 and 120. It is envisioned that the utilization of an over-the-center pivoting mechanism will enable the user to selectively compress the coil spring 131 a specific distance which, in turn, imparts a specific load on the reciprocating sleeve 134 which is converted to a rotational torque about the jaw pivot pin 95. As a result, a specific closure force can be transmitted to the opposing jaw members 110 and 120.

FIGS. 5A and 5B show the initial actuation of handle 40 towards fixed handle 50 which causes the pin 44 of flange 42 to move generally proximally and upwardly along entrance pathway 51. During movement of the flange 42 along the entrance pathway 51, respectively, the t-shaped pin 44 rides through passageway 53 along railway 55 as explained above. Once the desired position for the sealing site is determined and the jaw members 110 and 120 are properly positioned, handle 40 may be compressed fully such that the t-shaped pin 44 of flange 42 seats within catch basin 55'. Once pin 44 clears an edge or passes a predetermined point in the passageway 53 at the edge of the catch basin 55', releasing movement of the handle 40 and flange 42 is redirected into a catch basin 55'.

More particularly, upon a slight reduction in the closing pressure of handle 40 against handle 50, the handle 40 returns slightly distally towards entrance pathway 51 but is re-directed to seat within catch basin 55'. At this point, the release or return pressure between the handles 40 and 50 which is attributable and directly proportional to the release pressure associated with the compression of the drive assembly 130 causes the pin 44 of flange 42 to settle or lock within catch basin 55'. Handle 40 is now secured in position within fixed handle 50 which, in turn, locks the jaw members 110 and 120 in a closed position against the tissue.

As mentioned above, the jaw members 110 and 120 may be opened, closed and rotated to manipulate tissue until sealing is desired. This enables the user to position and re-position the forceps 10 prior to activation and sealing. As illustrated in FIG. 1A, the end effector assembly 100 is rotatable about longitudinal axis "A-A" through rotation of the rotating assembly 80. As explained in more detail below, it is envisioned that the unique feed path of the cable leads 325a and 325b through the rotating assembly 80, along shaft 12 and, ultimately, to the jaw members 110 and 120 enables the user to rotate the end effector assembly 100 about 180 degrees across the clockwise and counterclockwise directions without tangling or causing undue strain on cable leads 325a and 325b. As can be appreciated, this facilitates the grasping and manipulation of tissue.

As best shown in FIGS. 5A, 5B, 6A, 9A, 9B, 11 and 12, trigger assembly 70 mounts atop movable handle 40 and cooperates with the knife assembly 160 to selectively translate knife 190 through a tissue seal. More particularly, the trigger assembly 70 includes a U-shaped finger actuator 71 having a pair upwardly-extending flanges 71a and 71b. A pivot pin 179 extends through a pair of apertures 162a and 162b in each of the flanges 71a and 71b, respectively, to mount the trigger assembly 70 to a knife carriage 165 as explained in more detail below. Finger actuator 71 is selectively pivotable within a pre-defined slot 21 disposed within housing 20 (See FIG. 6A). More particularly, a pair of pivots 77a and 77b is disposed on either side of the finger actuator 71 and are configured to mount between housing halves 20a and 20b to pivot the finger actuator within slot 21.

The knife assembly 160 includes a reciprocating knife bar 167 which mounts atop the drive sleeve 134 and between upwardly extending flanges 71a and 71b. Knife bar 167 includes a t-shaped proximal end 167' and a cuff 137 disposed at the distal end thereof. Cuff 137 is dimensioned to encapsulate drive sleeve 134 when the knife assembly 160 is assembled. A spring 76 biases the cuff in a proximal-most orientation. Proximal end 167' is dimensioned to mount and slidingly reciprocate within a slot 167" formed by housings 20a and 20b at assembly (See FIG. 12). A locking cap 137a and a mounting pin 179 secure the cuff 137 to the proximal end 193b of the knife rod 193 through aperture 197 disposed therein such that proximal movement to the finger actuator 71 results in distal movement of the knife bar 193. Cuff 137 and cap 137a also allow 360 degrees of rotation of the drive sleeve 134 therethrough.

As mentioned above, a knife carriage 165 mounts to the upwardly extending flanges 71a and 71b of the finger actuator 71. More particularly, the distal end 162 of the knife carriage 165 is t-shaped and includes two laterally extending pins 162c and 162d which engage apertures 162a and 162b, respectively, in flanges 71a and 71b. The proximal end 161 of the knife carriage 165 includes an aperture 161a defined therein which mates with a detent 167a which extends transversally through knife carriage 165.

As best illustrated in FIGS. 5A-7, when the handle 40 is disposed in a spaced-apart or open configuration relative to handle 50, flange 49' which extends from handle 40 prevents actuation of the trigger assembly 70. More particularly, finger actuator 71 is prevented from being actuated proximally by flange 49' when the jaw members 110 and 120 are open. As can be appreciated, this prevents premature actuation of the knife 190 when tissue is not grasped between jaw members 110 and 120. When handle 40 is selectively moved relative to handle 50, a gap 21 is formed between the flange 49' and the finger actuator 71 (See FIG. 5B). Thus, the user is free to selectively actuate the knife 190 by squeezing the finger actuator 71 proximally within gap 21.

Figure 6A:
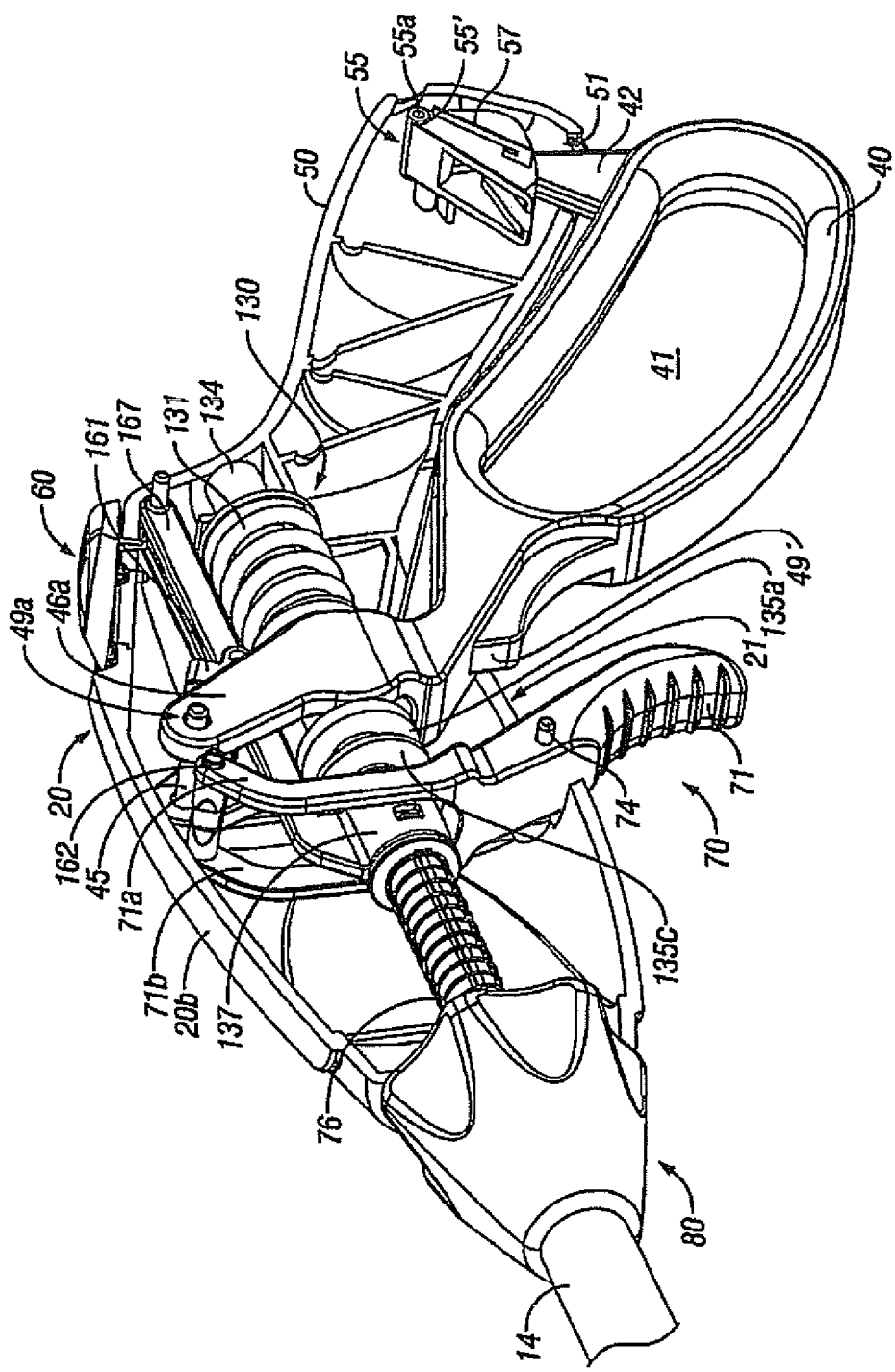
FIG. 6A is an internal, perspective view of the endoscopic forceps of FIG. 1B with the internal working components of the forceps exposed and the trigger shown in an un-actuated position.
Figure 6B:
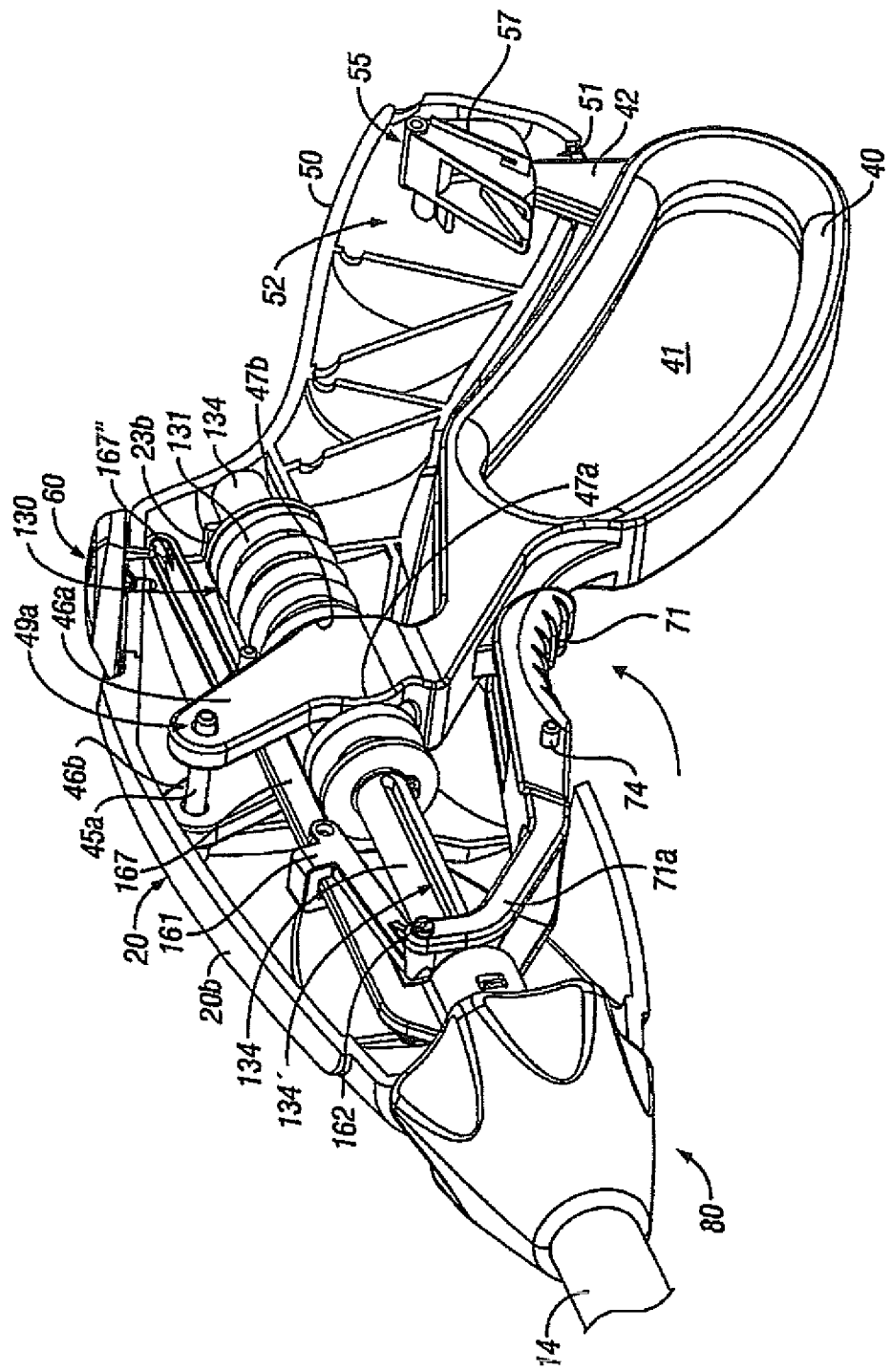
FIG. 6B is an internal, perspective view of the endoscopic forceps of FIG. 1B with the internal working components of the forceps exposed and the trigger shown in an actuated position.
Figure 6C:
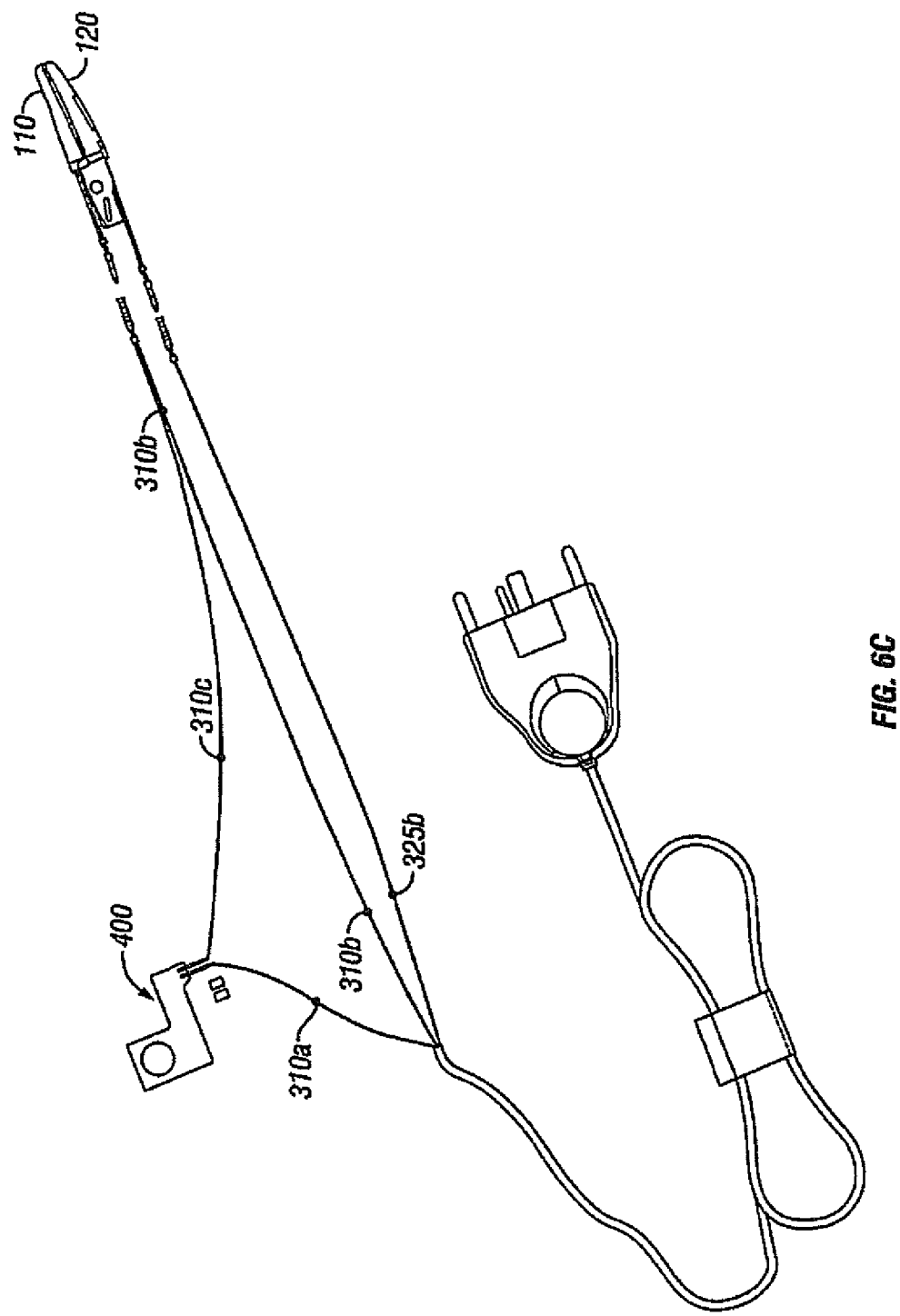
FIG. 6C is a schematic representation of the electrical configuration for the trigger assembly.
Figure 7:
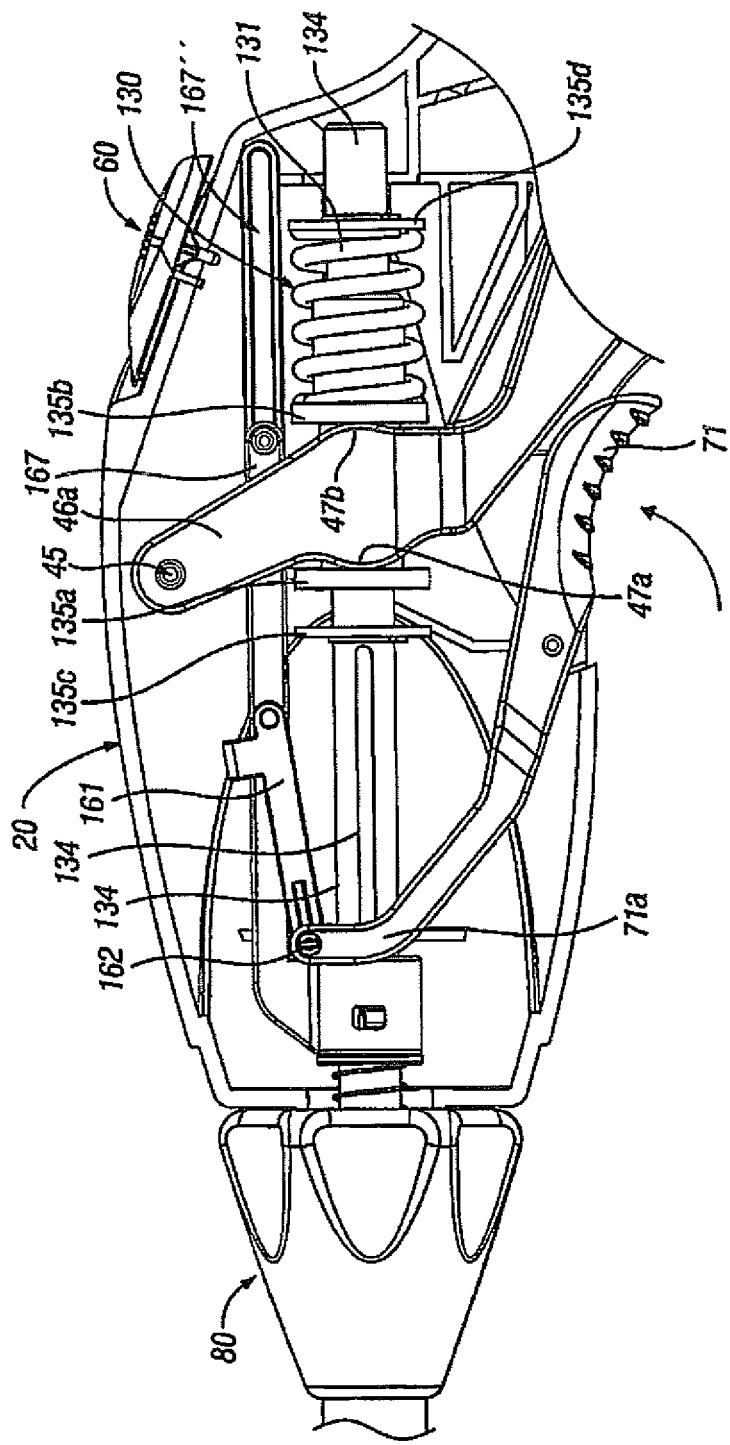
FIG. 7 is an internal, side view of the endoscopic forceps of FIG. 1B with the trigger shown in an actuated position.
Figure 8A:
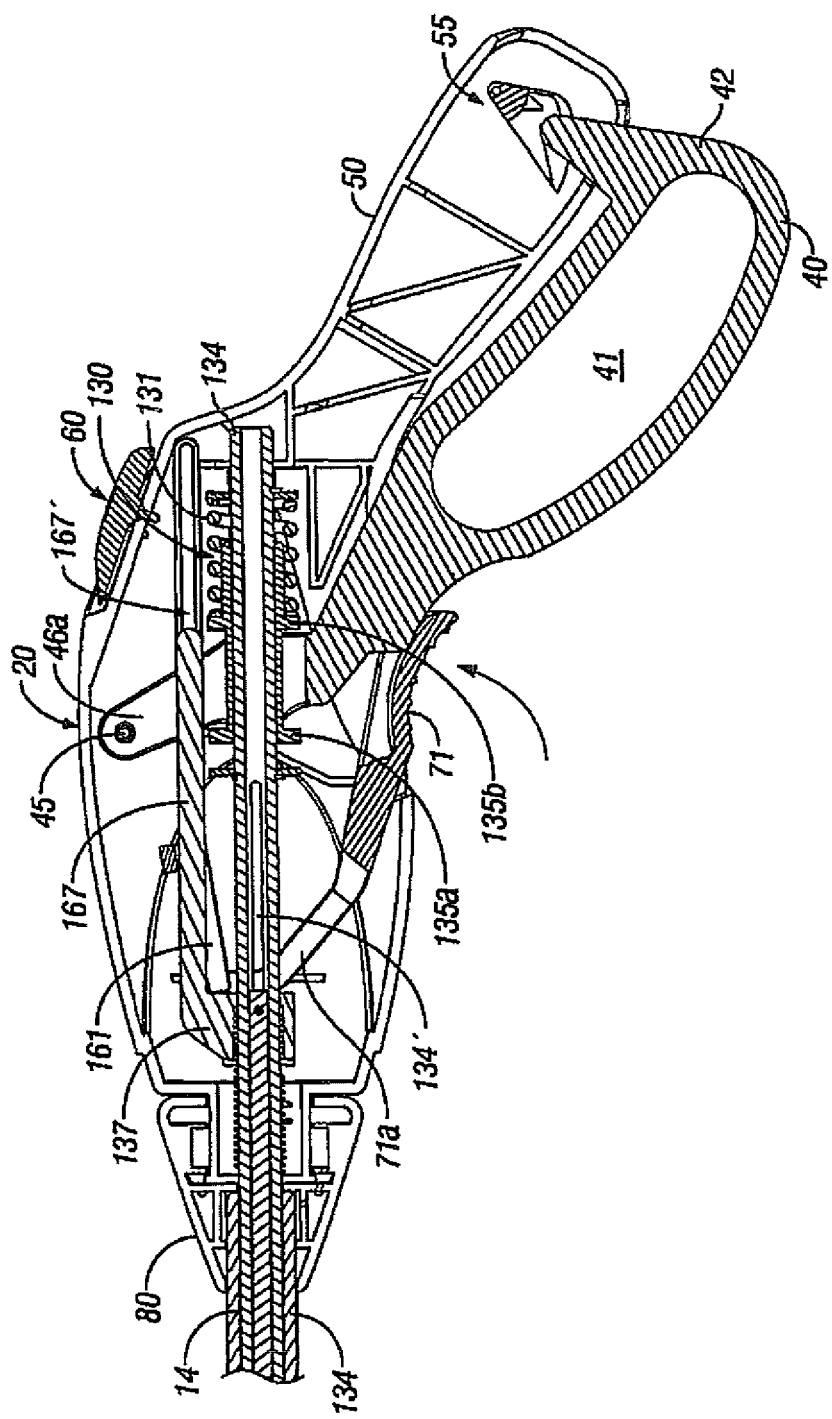
FIG. 8A is a side cross-sectional view showing the trigger in an actuated position.
Figure 9A:
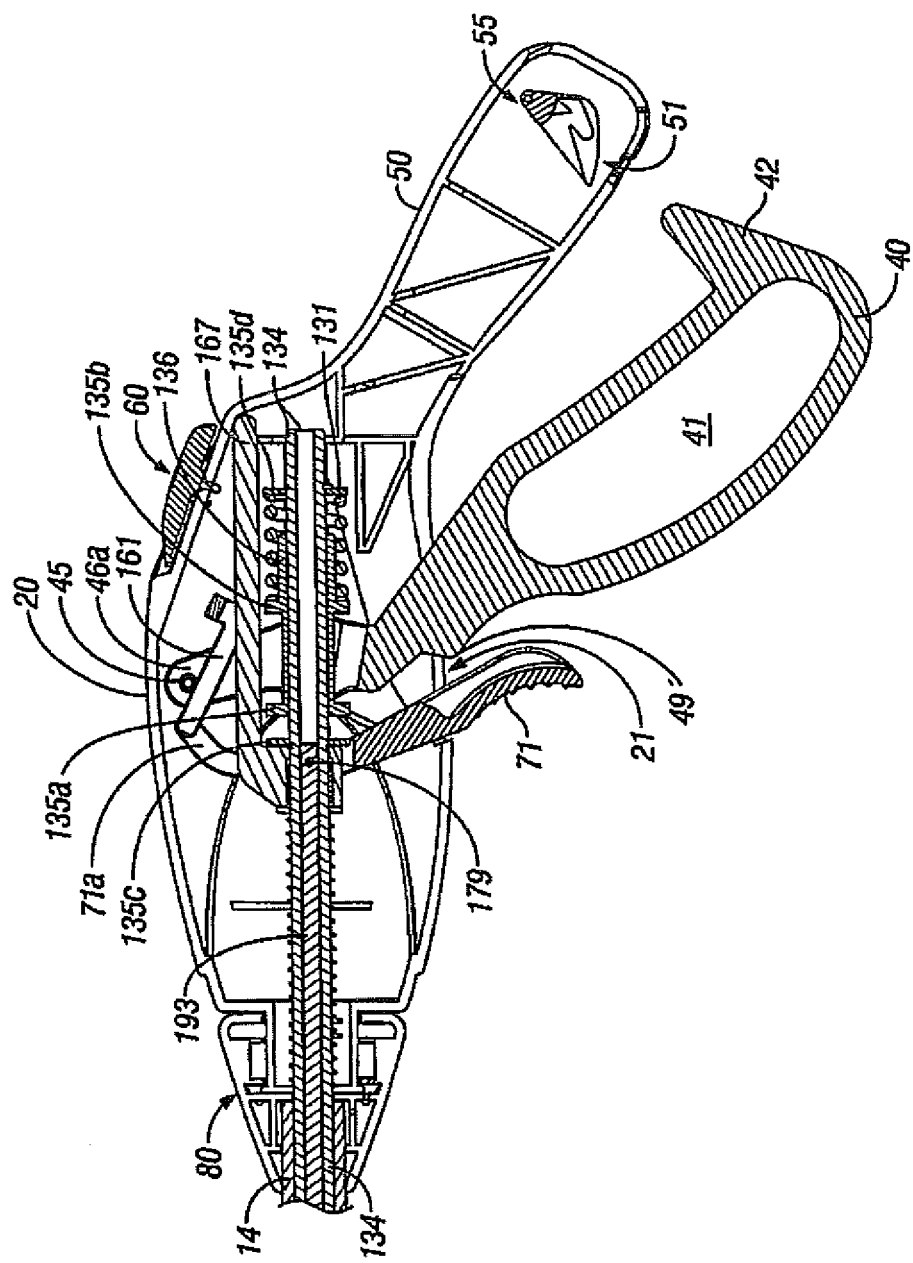
FIG. 9A is side cross-sectional view of the housing showing both the trigger and the handle un-actuated.
Figure 9B:
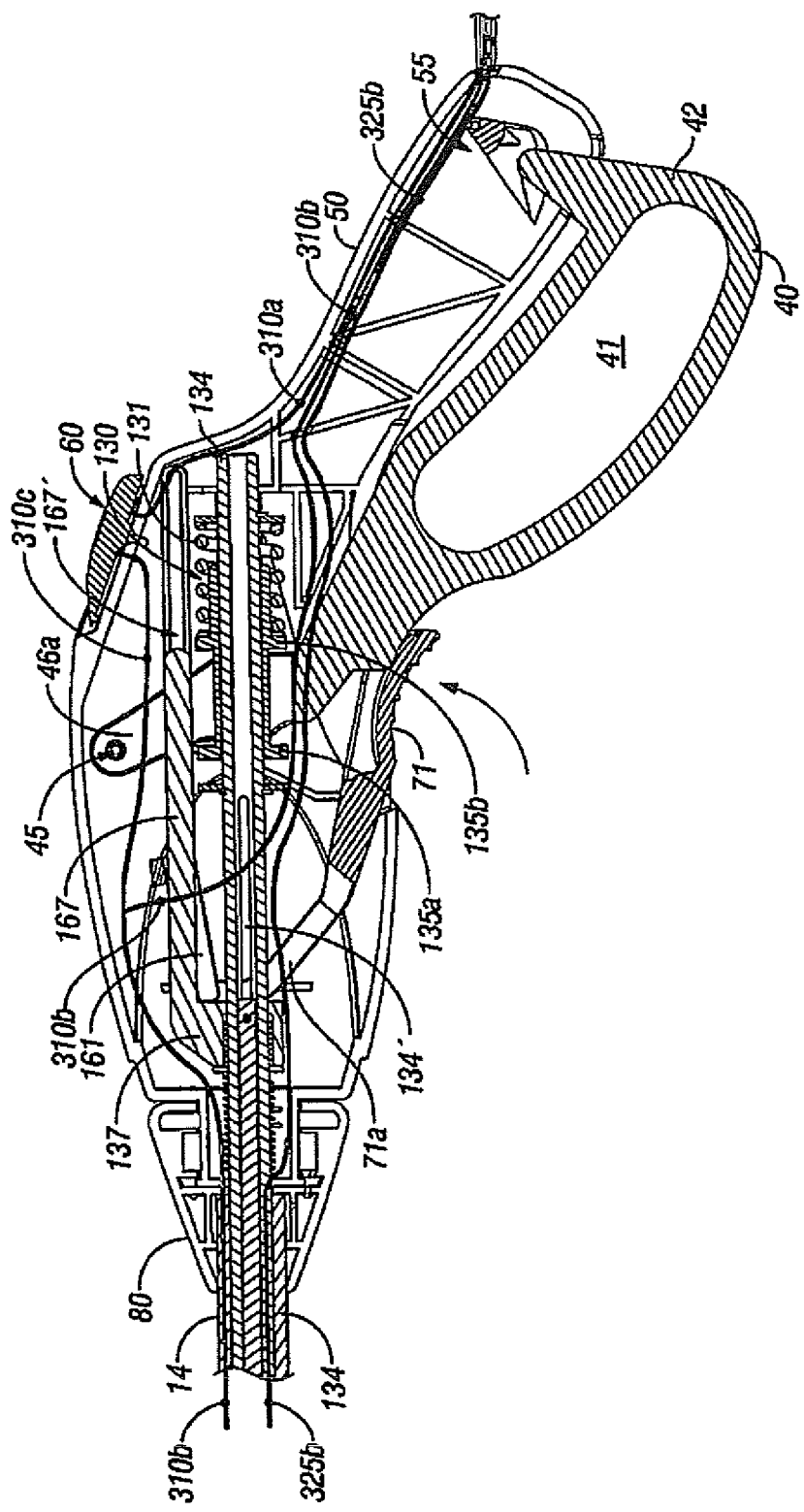
FIG. 9B is side cross-sectional view of the housing showing both the trigger and the handle actuated.
Figure 10C:
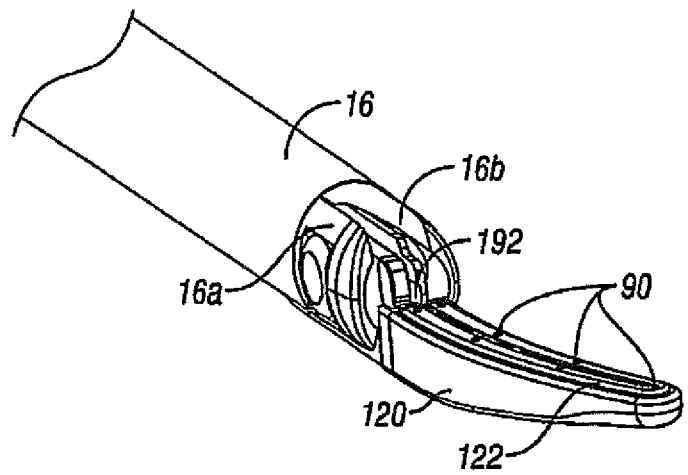
FIG. 10C is an enlarged, front perspective view of a bottom jaw member of the end effector assembly showing the knife in an unactuated position.
Figure 10D:
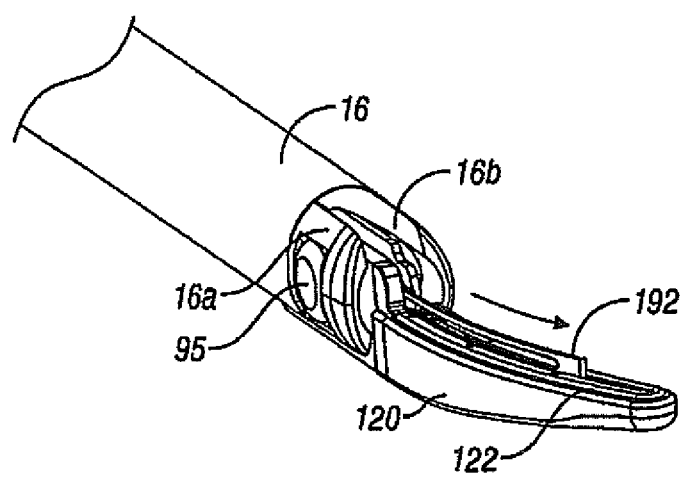
FIG. 10D is an enlarged, front perspective view of the bottom jaw member showing the knife in an actuated position.

As best shown in FIGS. 6B, 7 and 8A, once the clearance is provided by movement of handle 40, proximal movement of the finger actuator 71 about pivot 74 results in distal translation of the knife bar 167 which, in turn, results in distal translation of the knife rod 193 and knife 190. More particularly, when finger actuator 71 is squeezed proximally, the U-shaped flanges 71a and 71b rotate about pivot 74 to abut cuff 137 and essentially throw the knife carriage 165 forward which, in turn, carries the knife bar 167 forward to force the knife rod 193 distally. Slot 167" is configured to smoothly guide the knife bar 167 distally through the forward and return stroke. As shown in FIGS. 10A and 10B, distal translation of the knife rod 193 translates the knife 190 through channel 115 in the jaw members 110 and 120. As mentioned above, the knife rod 193 mounts the knife 190 via one or more mechanically interfacing elements or may be affixed in any known manner in the art. A slot 197 defined within the knife 190 provides clearance for pin 139 of the drive sleeve 134 during reciprocation of the knife 190. Upon release of finger actuator 71, spring 76 biases the knife assembly back to a proximal-most position. It is envisioned that the knife bar 167 provides variable mechanical advantage and linear advantage when triggering the knife 190. In addition, the incorporation of the knife bar 167 significantly reduces friction loss and provides smoother mechanical cutting than previously known methods.

Turning now in detail to the operation of the drive assembly as best seen in FIGS. 5A, 5B, 11 and 12, drive assembly 130 includes reciprocating sleeve 134, drive housing 135, spring 131, drive rings 135a and 135b, drive stops 135c and 135d and retaining rings 131' and 131" which all cooperate to form the drive assembly 130. It is envisioned that stop 135c may be removed and ring 131" would perform stop 135c's intended function. The proximal end 132 of the reciprocating sleeve 134 is positioned within an aperture 135' defined through the drive housing 135 to permit selective reciprocation of the drive sleeve 134 therethrough upon actuation of the movable handle 40. The spring 131 is assembled atop the drive housing 135 between a rear stop 135d and ring 135b such that movement handle 40 about pivot 45 moves the entire drive assembly 130 and sleeve 134 proximally which, in turn, pulls cam pin 139 proximally to close the jaw members 110 and 120. Once the jaw members 110 and 120 close about tissue, the drive assembly 130 essentially bottoms out (i.e., further proximal movement of the reciprocating sleeve is prevented) and further movement of handle 40 about pivot 45 compresses spring 131 resulting in additional closure force on the tissue. Moreover, spring 131 also tends to bias the jaw members 110 and 120 and the movable handle 40 in an open configuration.

Turning back to FIG. 12 which shows the exploded view of the housing 20, rotating assembly 80, trigger assembly 70, movable handle 40 and fixed handle 50, it is envisioned that all of these various component parts along with the shaft 12 and the end effector assembly 100 are assembled during the manufacturing process to form a partially and/or fully disposable forceps 10. For example and as mentioned above, the shaft 12 and/or end effector assembly 100 may be disposable and, therefore, selectively/releasably engageable with the housing 20 and rotating assembly 80 to form a partially disposable forceps 10 and/or the entire forceps 10 may be disposable after use.

As best seen in FIGS. 5A, 5B and 13, once assembled, spring 131 is poised for compression atop drive housing 135 upon actuation of the movable handle 40. More particularly, movement of the handle 40 about pivot pins 45a and 45b reciprocates the flange 42 into fixed handle 50 and forces drive assembly 130 to compress spring 131 against the rear stop 135d to reciprocate the sleeve 134.

As mentioned above, the trigger assembly 70 is initially prevented from firing by the locking flange 49' disposed on movable handle 40 which abuts against the trigger assembly 70 prior to actuation. It is envisioned that the opposing jaw members 110 and 120 may be rotated and partially opened and closed without unlocking the trigger assembly 70 which, as can be appreciated, allows the user to grip and manipulate the tissue without premature activation of the knife assembly 160. As mentioned below, only when the t-shaped pin 44 of flange 42 is completely reciprocated within channel 51 of the fixed handle 50 and seated within pre-defined catch basin 55' will the locking flange 49' allow full activation of the trigger assembly 70. The operating features and relative movements of these internal working components of the forceps 10 are shown by phantom representation and directional arrows and are best illustrated in the various figures.

It is envisioned that the mechanical advantage of the over-the-center pivot will enable the user to selectively compress the coil spring 131 a specific distance which, in turn, imparts a specific load on the reciprocating sleeve 134.

The reciprocating sleeve's 134 load is converted to a torque about the jaw pivot 95. As a result, a specific closure force can be transmitted to the opposing jaw members 110 and 120. As mentioned above, the jaw members 110 and 120 may be opened, closed and rotated to manipulate tissue until sealing is desired without unlocking the trigger assembly 70. This enables the user to position and re-position the forceps 10 prior to activation and sealing. More particularly, as illustrated in FIG. 1A, the end effector assembly 100 is rotatable about longitudinal axis "A-A" through rotation of the rotating assembly 80.

Once the desired position for the sealing site is determined and the jaw members 110 and 120 are properly positioned, handle 40 may be compressed fully such that the t-shaped pin 44 of flange 42 clears a pre-defined railway edge located atop the railway 55. Once end 44 clears the railway edge, the end 44 is directed into catch basin 55' to lock the handle 40 relative to handle 50. The release or return pressure between the handles 40 and 50 which is attributable and directly proportional to the release pressure associated with the compression of the drive assembly 130 causes the end 44 of flange 42 to settle or lock within catch basin 55'. Handle 40 is now secured in position within fixed handle 50 which, in turn, locks the jaw members 110 and 120 in a closed position against the tissue.

At this point the jaws members 110 and 120 are fully compressed about the tissue. Moreover, the forceps 10 is now ready for selective application of electrosurgical energy and subsequent separation of the tissue, i.e., as t-shaped end 44 seats within catch basin 55', locking flange 49' moves into a position to permit activation of the trigger assembly 70.

As the t-shaped end 44 of flange 42 seats within catch basin 55', a proportional axial force on the reciprocating sleeve 134 is maintained which, in turn, maintains a compressive force between opposing jaw members 110 and 120 against the tissue. It is envisioned that the end effector assembly 100 and/or the jaw members 110 and 120 may be dimensioned to off-load some of the excessive clamping forces to prevent mechanical failure of certain internal operating elements of the end effector 100.

As can be appreciated, the combination of the mechanical advantage of the over-the-center pivot along with the compressive force associated with the compression spring 131 facilitate and assure consistent, uniform and accurate closure pressure about the tissue within the desired working pressure range of about 3 kg/cm$^2$ to about 16 kg/cm$^2$ and, desirably, about 7 kg/cm$^2$ to about 13 kg/cm$^2$. By controlling the intensity, frequency and duration of the electrosurgical energy applied to the tissue, the user can treat tissue, i.e., seal tissue.

As mentioned above, two mechanical factors play an important role in determining the resulting thickness of the sealed tissue and effectiveness of the seal, i.e., the pressure applied between opposing jaw members 110 and 120 and the gap distance "G" between the opposing sealing surfaces 112, 122 of the jaw members 110 and 120 during the sealing process. However, thickness of the resulting tissue seal cannot be adequately controlled by force alone. In other words, too much force and the two jaw members 110 and 120 would touch and possibly short resulting in little energy traveling through the tissue thus resulting in a bad tissue seal 450. Too little force and the seal would be too thick.

Applying the correct force is also important for other reasons: to oppose the walls of the vessel; to reduce the tissue impedance to a low enough value that allows enough current through the tissue; and to overcome the forces of expansion during tissue heating in addition to contributing towards creating the required end tissue thickness which is an indication of a good seal.

In one embodiment, the electrically conductive sealing surfaces 112 and 122 of the jaw members 110 and 120, respectively, are relatively flat to avoid current concentrations at sharp edges and to avoid arcing between high points. In addition and due to the reaction force of the tissue when engaged, jaw members 110 and 120 can be manufactured to resist bending. For example, the jaw members 110 and 120 may be tapered along the width thereof which is advantageous for two reasons: 1) the taper will apply constant pressure for a constant tissue thickness at parallel; 2) the thicker proximal portion of the jaw members 110 and 120 will resist bending due to the reaction force of the tissue.

As mentioned above, at least one jaw member, e.g., 120, may include one or more stop members 90 which limit the movement of the two opposing jaw members 110 and 120 relative to one another. In one embodiment, the stop members 90 extend from the sealing surface 122 a predetermined distance according to the specific material properties (e.g., compressive strength, thermal expansion, etc.) to yield a consistent and accurate gap distance "G" during sealing (FIG. 10B). It is envisioned for the gap distance between opposing sealing surfaces 112 and 122 during sealing ranges from about 0.001 inches to about 0.006 inches and, desirably, between about 0.002 and about 0.005 inches. In one embodiment, the non-conductive stop members 90 are molded onto the jaw members 110 and 120 (e.g., overmolding, injection molding, etc.), stamped onto the jaw members 110 and 120 or deposited (e.g., deposition) onto the jaw members 110 and 120. For example, one technique involves thermally spraying a ceramic material onto the surface of the jaw member 110 and 120 to form the stop members 90. Several thermal spraying techniques are contemplated which involve depositing a broad range of heat resistant and insulative materials on various surfaces to create stop members 90 for controlling the gap distance between electrically conductive surfaces 112 and 122.

As energy is being selectively transferred to the end effector assembly 100, across the jaw members 110 and 120 and through the tissue, a tissue seal forms isolating two tissue halves. At this point and with other known vessel sealing instruments, the user may remove and replace the forceps 10 with a cutting instrument (not shown) to divide the tissue halves along the tissue seal. As can be appreciated, this is both time consuming and tedious and may result in inaccurate tissue division across the tissue seal due to misalignment or misplacement of the cutting instrument along the ideal tissue cutting plane.

As explained in detail above, the present disclosure incorporates knife assembly 160 which, when activated via the trigger assembly 70, progressively and selectively divides the tissue along an ideal tissue plane in a precise manner to effectively and reliably divide the tissue into two sealed halves. The knife assembly 160 allows the user to quickly separate the tissue immediately after sealing without substituting a cutting instrument through a cannula or trocar port. As can be appreciated, accurate sealing and dividing of tissue is accomplished with the same forceps 10.

It is envisioned that knife blade 190 may also be coupled to the same or an alternative electrosurgical energy source to facilitate separation of the tissue along the tissue seal. Moreover, it is envisioned that the angle of the trip of the knife blade 190 may be dimensioned to provide more or less aggressive cutting angles depending upon a particular purpose. For example, the knife blade 190 may be positioned at an angle which reduces "tissue wisps" associated with cutting. Moreover, the knife blade 190 may be designed having different blade geometries such as serrated, notched, perforated, hollow, concave, convex etc. depending upon a particular purpose or to achieve a particular result. It is envisioned that the knife assembly 160 generally cuts in a progressive, uni-directional fashion (i.e., distally).

Once the tissue is divided into tissue halves, the jaw members 110 and 120 may be opened by re-grasping the handle 40 as explained below. Re-initiation or re-grasping of the handle 40 again moves t-shaped pin 44 of flange 42 generally proximally.

As best shown in FIG. 13, the proximal portions of the jaw members 110 and 120 and the distal end 16 of shaft 12 may be covered by a resilient or flexible insulating material 185 to reduce stray current concentrations during electrosurgical activation. An insulating boot (not shown) may also be positioned atop the proximal portions of the jaw members 110 and 120 to further reduce current concentrations and stray currents from damaging adjacent tissue. Details relating to one envisioned insulating boot 220 are described with respect to commonly-owned U.S. Provisional Application Ser. No. 60/722,213 entitled "INSULATING BOOT FOR ELECTROSURGICAL FORCEPS", the entire contents of which being incorporated by reference herein.

Switch 60 is ergonomically dimensioned and conforms to the outer shape of housing 20 (once assembled). Switch 60 is designed to electromechanically cooperate with a flex circuit 400 to allow a user to selectively activate the jaw members 110 and 120. It is contemplated that a flex circuit design facilitates manufacturing due to the circuit unique ability to conform as needed into tightly spaced areas. It is also envisioned that the switch 60 permits the user to selectively activate the forceps 10 in a variety of different orientations, i.e., multi-oriented activation or toggle-like activation. As can be appreciated, this simplifies activation. It is envisioned that switch 60 may also be designed as a so called "dome switch" which also provides tactile feedback to the user when activated.

When switch 60 is depressed, trigger lead 310*b* carries the first electrical potential to jaw member 110 thus completing a bipolar circuit. More particularly, when switch 60 is depressed and flex circuit 400 is activated, the generator recognizes a voltage drop across leads 310*a* and 310*c* which initiates activation of the generator to supply a first electrical potential to jaw member 110 and a second electrical potential to jaw member 120. Switch 60 acts as a control circuit and is protected or removed from the actual current loop which supplies electrical energy to the jaw members 110 and 120. This reduces the chances of electrical failure of the switch 60 due to high current loads during activation. A footswitch (not shown) which may also be utilized with the forceps 10, also operates in a similar manner, i.e., upon activation of the footswitch, the generator recognizes a voltage drop across the input and output leads of the footswitch which, in turn, signals the generator to initiate electrosurgical activation of the jaw members 110 and 120.

It is envisioned that a safety switch or circuit (not shown) may be employed such that the switch cannot fire unless the jaw members 110 and 120 are closed and/or unless the jaw members 110 and 120 have tissue held therebetween.

In the latter instance, a sensor (not shown) may be employed to determine if tissue is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. Various sensor mechanisms and feedback systems are described in commonly-owned, co-pending U.S. patent application Ser. No. 10/427,832 entitled "METHOD AND SYSTEM FOR CONTROLLING OUTPUT OF RF MEDICAL GENERATOR" filed on May 1, 2003 the entire contents of which are hereby incorporated by reference herein.

The jaw members 110 and 120 are electrically isolated from one another such that electrosurgical energy can be effectively transferred through the tissue to form seal. The cable leads 310*b* and 325*b* are held loosely but securely along the cable path to permit rotation of the jaw members 110 and 120 about longitudinal axis "A" (See FIG. 1A). More particularly, cable leads 310*b* and 325*b* are fed through respective halves 80*a* and 80*b* of the rotating assembly 80 in such a manner to allow rotation of the shaft 12 (via rotation of the rotating assembly 80) in the clockwise or counter-clockwise direction without unduly tangling or twisting the cable leads 310*b* and 325*b*. The presently disclosed cable lead feed path is envisioned to allow rotation of the rotation assembly approximately 180 degrees in either direction.

Figure 15A:
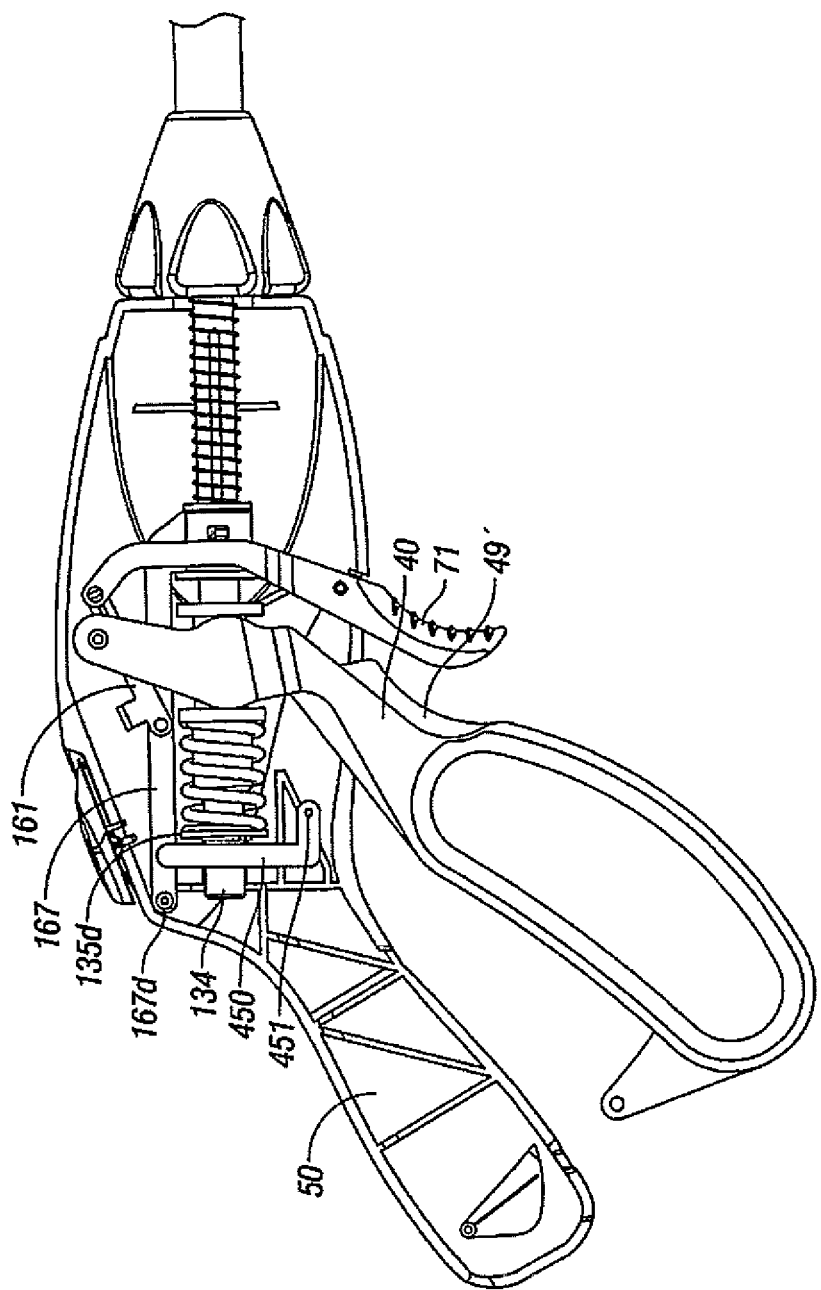
FIG. 15A is an internal view of one embodiment of the forceps of the present disclosure having a knife assembly lockout mechanism shown in an engaged position.
Figure 15B:
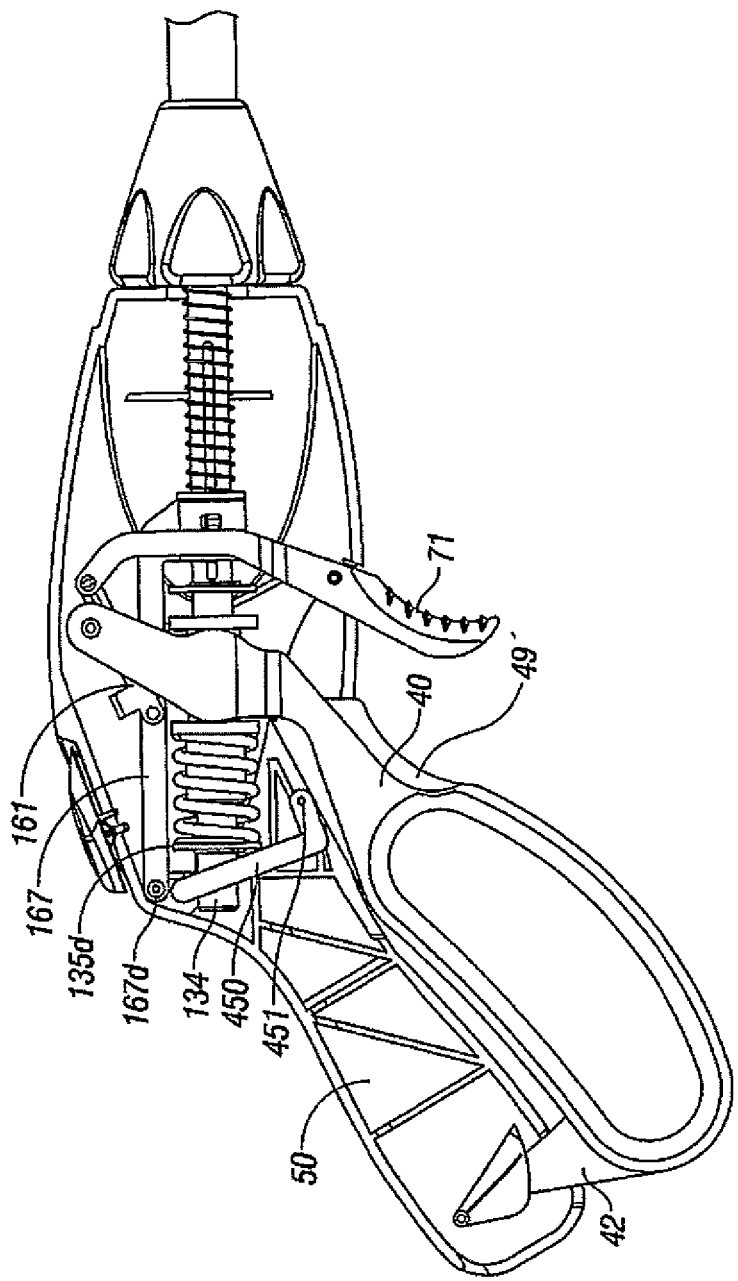
FIG. 15B is an internal view of the forceps of FIG. 15A showing the knife assembly lockout mechanism in a disengaged position.

As best shown in FIGS. 15A and 15B, the forceps 10 may include a different knife assembly lockout mechanism 450 which operates independently of or in conjunction with lockout flange 49'. As mentioned above, the lockout flange 49' prevents actuation of the knife assembly 70 when handle 40 is disposed in an open orientation as shown best ion FIG. 5A. Knife assembly lockout mechanism 450 actively disengages upon movement of the handle 40 from an open configuration (FIG. 15A) to a closer configuration (15B). More particularly, when the handle 40 is disposed in an open configuration, lockout mechanism 450 is normally biased to obstruct the movement of t-shaped proximal end 167*d* of the knife bar 167 within slot 167" defined in the housing 20 thereby preventing the knife bar 167 from moving distally.

Upon movement of the handle from the open configuration to a closer or closed configuration, the drive stop 135*d* (disposed about drive sleeve 134) is forced proximally which, in turn, forces lockout mechanism 450 to rotate about a pivot 451 out of obstructive alignment with the t-shaped proximal end 167*d* of the knife bar 167 (See FIG. 15B). The knife bar 167 is now unencumbered for selective actuation by the user. A spring 452 (shown schematically) may be included to bias the lockout mechanism 450 in a normally engaged, obstructive orientation. As can be appreciated, lockout mechanism 450 assures that the knife assembly 70 cannot be actuated unless the handle 40 is disposed in a closed position.

Figure 16A:
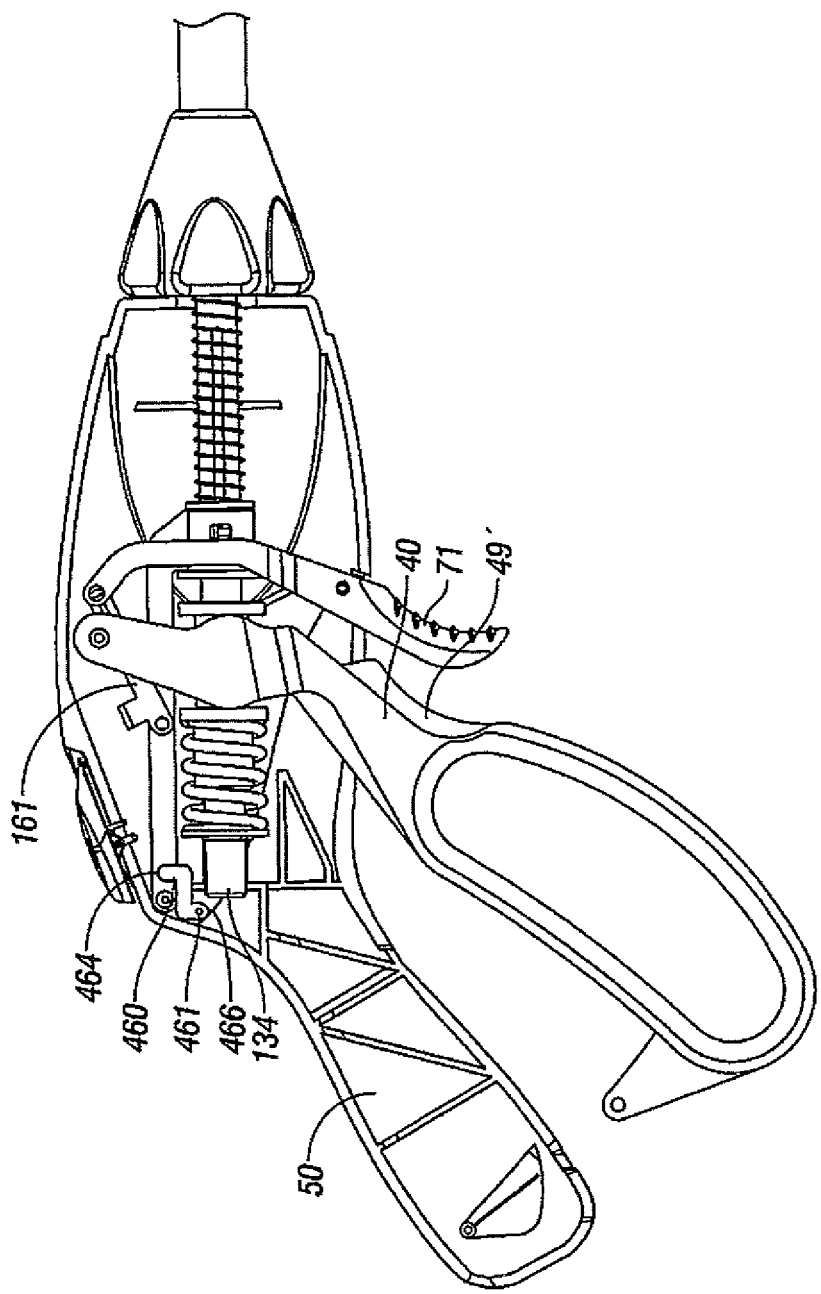
FIG. 16A is an internal view of another embodiment of the forceps of the present disclosure having an alternative knife assembly lockout mechanism shown in an engaged position.
Figure 16B:
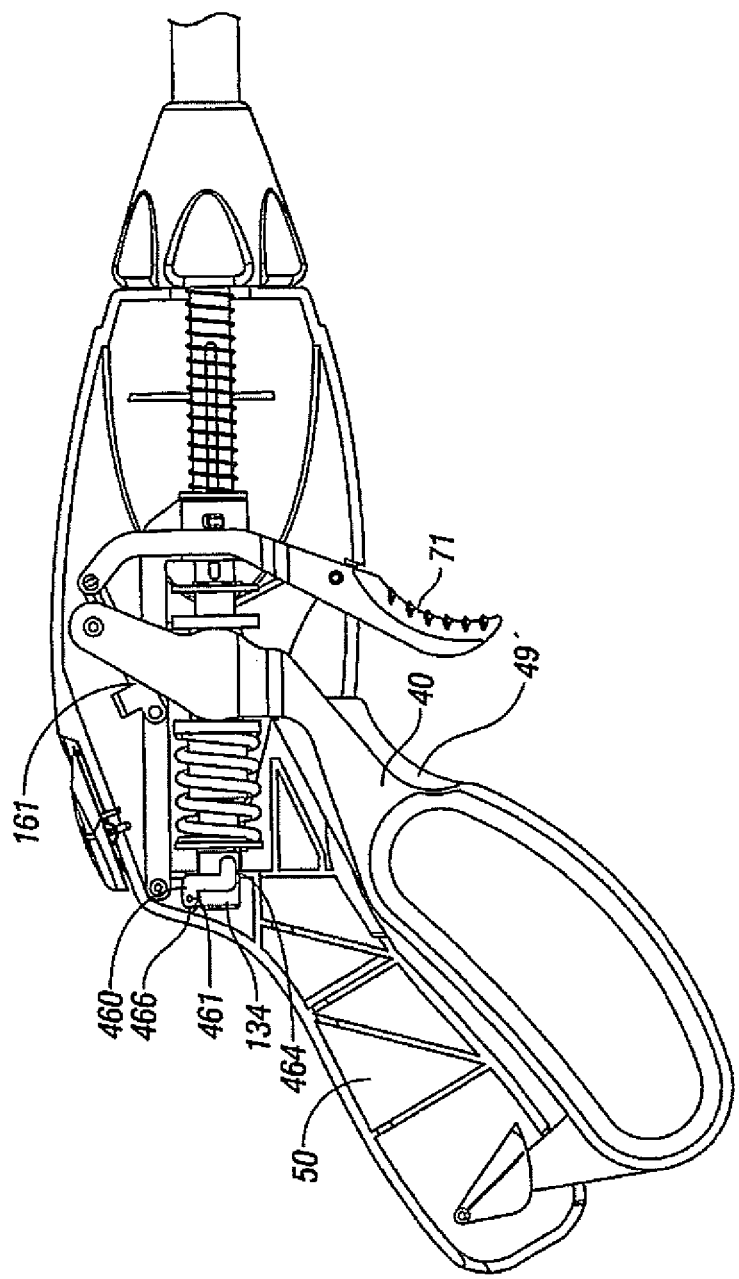
FIG. 16B is an internal view of the forceps of FIG. 15A showing the alternative knife assembly lockout mechanism in a disengaged position.

As best shown in FIGS. 16A and 16B, the forceps 10 may include still yet another type of knife assembly lockout mechanism 460 which also operates independently of or in conjunction with lockout flange 49'. Lockout mechanism 460 is generally hook-like and includes upper and lower hook elements 464 and 466, respectively. Lockout mechanism 460 actively disengages upon movement of the handle 40 from an open configuration (FIG. 16A) to a closer configuration (16B). More particularly, when the handle 40 is disposed in an open configuration, lockout mechanism 460 is normally biased to obstruct the movement of t-shaped proximal end 167*d* of the knife bar 167 within slot 167" defined in the housing 20 thereby preventing the knife bar 167 from moving distally.

Upon movement of the handle from the open configuration to a closer or closed configuration, the drive sleeve 134 is forced proximally which, in turn, forces lockout mechanism 460 to rotate about a pivot 461 such that upper hook-like element 164 dislodges out of obstructive alignment with the t-shaped proximal end 167d of the knife bar 167 (See FIG. 16B). The knife bar 167 is now unencumbered for selective actuation by the user. A spring 462 (shown schematically) may be included to bias the lockout mechanism 460 in a normally engaged, obstructive orientation. As can be appreciated, lockout mechanism 460 assures that the knife assembly 70 cannot be actuated unless the handle 40 is disposed in a closed position.

From the foregoing and with reference to the various figure drawings, those skilled in the art will appreciate that certain modifications can also be made to the present disclosure without departing from the scope of the same. For example, it may be preferable to add other features to the forceps 10, e.g., an articulating assembly to axially displace the end effector assembly 100 relative to the elongated shaft 12.

It is also contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue grasped between the jaw members 110 and 120. The sensor or feedback mechanism may also measure the impedance across the tissue during sealing and provide an indicator (visual and/or audible) that an effective seal has been created between the jaw members 110 and 120. Examples of such sensor systems are described in commonly-owned U.S. patent application Ser. No. 10/427,832 entitled "METHOD AND SYSTEM FOR CONTROLLING OUTPUT OF RF MEDICAL GENERATOR" filed on May 1, 2003 the entire contents of which are hereby incorporated by reference herein.

Moreover, it is contemplated that the trigger assembly 70 may include other types of recoil mechanism which are designed to accomplish the same purpose, e.g., gas-actuated recoil, electrically-actuated recoil (i.e., solenoid), etc. It is also envisioned that the forceps 10 may be used to cut tissue without sealing. Alternatively, the knife assembly 70 may be coupled to the same or alternate electrosurgical energy source to facilitate cutting of the tissue.

It is envisioned that the outer surface of the end effector assembly 100 may include a nickel-based material, coating, stamping, metal injection molding which is designed to reduce adhesion between the jaw members 110 and 120 with the surrounding tissue during activation and sealing. Moreover, it is also contemplated that the conductive surfaces 112 and 122 of the jaw members 110 and 120 may be manufactured from one (or a combination of one or more) of the following materials: nickel-chrome, chromium nitride, Med-Coat 2000 manufactured by The Electrolizing Corporation of OHIO, inconel 600 and tin-nickel. The tissue conductive surfaces 112 and 122 may also be coated with one or more of the above materials to achieve the same result, i.e., a "non-stick surface". As can be appreciated, reducing the amount that the tissue "sticks" during sealing improves the overall efficacy of the instrument.

One particular class of materials disclosed herein has demonstrated superior non-stick properties and, in some instances, superior seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 112 and 122 made from or coated with Ni200, Ni201 (~100% Ni) also showed improved non-stick performance over typical bipolar stainless steel electrodes.

As can be appreciated, locating the switch 60 on the forceps 10 has many advantages. For example, the switch 60 reduces the amount of electrical cable in the operating room and eliminates the possibility of activating the wrong instrument during a surgical procedure due to "line-of-sight" activation. Moreover, it is also envisioned that the switch 60 may be configured such that it is mechanically or electro-mechanically decommissioned during trigger activation to eliminate unintentionally activating the device during the cutting process. It is also envisioned that the switch 60 may be disposed on another part of the forceps 10, e.g., the fixed handle 50, rotating assembly 80, housing 20, etc.

It is also envisioned that the forceps 10 may be equipped with an automatic, electro-mechanical release mechanism (not shown) which releases the tissue once an end seal is determined (i.e., end-tone signal from the generator). For example, an electromechanical interface may be configured to automatically release the t-shaped pin 44 from catch basin 55 upon an end tone condition.

It is also contemplated that the forceps 10 may be dimensioned to include a trigger assembly 70 which operates in lieu of the switch assembly 60 to activate the forceps to seal tissue while also advancing the knife 190 to divide the tissue across the seal. For example, the trigger assembly 70 could be configured to have two stages: a first or initial stroke stage which activates the generator to selectively seal tissue; and a second or subsequent stage which advances the knife through the tissue. Alternatively, another embodiment may include a trigger assembly which simultaneously activates the jaw members 110 and 120 to seal tissue and advances the knife 190 through the tissue during activation. The trigger assembly may also be configured to move the knife assembly (or one or more of the components thereof) proximally to cut tissue disposed between the jaw members.

It is also envisioned that the rotating assembly 80 may be equipped with one or more mechanical interfaces which are rotatable with or within the rotating assembly 80 and which are configured to produce tactile and/or audible feedback to the user during rotation. The tactile and/or audible feedback (i.e., a "click") may be configured to correspond to a particular degree of rotation of the end effector assembly 100 about the axis "A". It is also contemplated that one or more types of visual indicia may also be employed with the rotating assembly 80 to correspond to the amount or degree of rotation of the end effector assembly 100 and may be designed correspond to or relate to the audible and/or tactile feedback depending upon a particular purpose.

Another envisioned version of the forceps 10 may include a telescoping shaft which allows the user to selectively regulate the length of the instrument for particular surgical purposes. For example, it is envisioned that the shaft may include two slidingly reciprocatable and extendible elements which upon exertion (i.e., pulling, twisting, or by virtue of a mechanical lever on the handle) either lengthen or shorten the size of the elongated shaft 12 depending upon a particular surgical purpose.

Moreover, it is also contemplated that the diameter of shaft 12 may be selectively expandable depending upon a particular surgical purpose or to provide rigidity of the forceps 10 inside the surgical cavity or to enhance the sealing effect of the shaft through a trocar. More particularly, it is contemplated that the shaft 12 may be configured to expand upon exertion (i.e., twisting or rotating one element inside another (iris-like), sliding a mechanical lever, an inflatable system, a mechanically expanding system or other types of known expansion systems). As a result, the surgeon can selectively expand the outer diameter of the shaft 12 to enhance the rigidity of the shaft 12 within a trocar and/or enhance the sealing effect of the shaft 12 within the trocar to reduce the possibility of pressure leakage from surgical cavity during use. Moreover, a single forceps may be selectively adaptable to work with differently-sized trocars and/or cannulas which may prove advantageous for particular operations and other surgical procedures.

It is also contemplated that the forceps 10 may be configured such that handle 50 is selectively replaceable or selectively positionable depending upon user preference. For example, handle 50 may be selectively detached and replaced with another handle 50 which is of different dimension (i.e., size, weight, angle, orientation to user's hand, etc.) which facilitates handling during surgical procedures. Alternatively, handle 50 may be selectively positionable relative to the housing 20 (i.e., the angle of the handle to the housing is adjustable) to facilitate handling and use during particular surgical procedures or for user comfort.

It is also envisioned that the forceps may be configure to include a visual indicator (which cooperates with the "end tone" indicator on the generator) to provide visual confirmation of a successful seal (e.g., a green LED indicator). The visual indicator (not shown) may be employed on or in connection with the end effector assembly 100 or shaft 12 which is in line-of-site of the surgeon during use. The visual indicator may also be designed to warn the user of a mis-seal condition or a re-grasp condition (e.g., a red LED indicator). Alternatively, the visual indicator may also be configured to provide progressive feedback of the formation of the seal during the sealing process. For example, a series of LEDs may be employed on the end effector assembly 100 (or shaft 12) which progressively illuminate through the sealing process to provide visual feedback to the user regarding the status of the seal.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. An endoscopic bipolar forceps, comprising:
    a housing;
    a shaft extending from the housing defining a longitudinal axis;
    first and second jaw members supported at a distal end of the shaft and capable of conducting electrosurgical energy to tissue held therebetween to effect a tissue seal, at least one of the first and second jaw members moveable relative to the other from a first position wherein the first and second jaw members are disposed in spaced relation relative to one another to a second position wherein the first and second jaw members are closer to one another for manipulating tissue;
    a moveable handle rotatable about a pivot to move the first and second jaw members between the first and second position, the pivot located a fixed distance above the longitudinal axis;
    a knife assembly having a knife bar configured to move a knife to cut tissue disposed between the first and second jaw members, the knife bar including a generally t-shaped proximal end dimensioned to operatively engage a corresponding slot defined within the housing, the slot guiding movement of the knife bar during translation thereof; and
    a knife lockout mechanism operatively connected to the moveable handle wherein movement of the moveable handle moves the knife lockout mechanism from a first orientation to a second orientation, wherein in the first orientation the knife lockout mechanism prevents the knife bar from moving, and wherein in the second orientation the knife lockout mechanism allows selective, unencumbered movement of the knife bar to cut tissue disposed between the first and second jaw members.

2. The endoscopic bipolar forceps according to claim 1, further comprising a drive stop operatively engaged with the knife lockout mechanism such that rotation of the moveable handle causes the drive stop to move the knife lockout mechanism between the first orientation and the second orientation.

3. The endoscopic bipolar forceps according to claim 1, wherein the knife lockout mechanism obstructs the t-shaped proximal end of the knife bar when disposed in the first orientation.

4. The endoscopic bipolar forceps according to claim 1, wherein the knife bar is operatively coupled to the knife slidingly disposed within the shaft.

5. The endoscopic bipolar forceps according to claim 4, further comprising a finger actuator operatively coupled to the knife assembly wherein movement of the finger actuator moves the knife bar which, in turn, moves the knife to cut tissue disposed between the jaw members.

6. The endoscopic bipolar forceps according to claim 1, further comprising a spring which biases the knife assembly in a proximal-most orientation.

7. The endoscopic bipolar forceps according to claim 1, further comprising a spring which biases the knife lockout mechanism towards the first orientation.

8. The endoscopic bipolar forceps according to claim 1, further comprising a hand switch disposed within the housing and adapted to connect to a source of electrosurgical energy, the hand switch allowing a user to selectively supply electrosurgical energy to the first and second jaw members to effect a tissue seal.

9. The endoscopic bipolar forceps according to claim 1, wherein at least one of the first and second jaw members includes a series of stop members disposed thereon configured to regulate the distance between the first and second jaw members during sealing.

10. An endoscopic bipolar forceps, comprising:
    a housing;
    a shaft affixed to the housing having a longitudinal axis defined therethrough;
    first and second jaw members at a distal end of the shaft electrically connected to a source of electrosurgical energy through the shaft such that the first and second jaw members are capable of conducting energy through tissue held therebetween to effect a tissue seal;
    a selectively translatable drive sleeve configured to transition at least one of the first and second jaw members relative to the other between a first position wherein the first and second jaw members are disposed in spaced relation relative to one another and a second position wherein the first and second jaw members are closer to one another for manipulating tissue;
- a movable handle rotatable about a pivot to move the drive sleeve to transition the first and second jaw members between the first and second positions, the pivot located a fixed distance above the longitudinal axis;
- a knife assembly having a knife bar with a t-shaped proximal end, said knife assembly selectively movable to advance the knife bar which, in turn, moves a knife to cut tissue between jaw members; and
- a knife lockout mechanism operatively coupled to the drive sleeve wherein translation of the drive sleeve pivots the knife lockout mechanism between a first orientation in obstructive relationship with the t-shaped proximal end of the knife bar to prevent movement thereof to a second orientation which allows selective, unencumbered movement of the t-shaped proximal end of the knife bar to reciprocate the knife to cut tissue disposed between the jaw members.

11. An endoscopic bipolar forceps, comprising:
- a housing;
- a shaft affixed to the housing having a longitudinal axis defined therethrough;
- first and second jaw members at a distal end of the shaft electrically connected to a source of electrosurgical energy through the shaft such that the first and second jaw members are capable of conducting energy through tissue held therebetween to effect a tissue seal;
- a selectively translatable drive sleeve configured to move at least one of the first and second jaw members relative to the other from a first position wherein the jaw members are disposed in spaced relation relative to one another to a second position wherein the jaw members are closer to one another for manipulating tissue;
- a movable handle rotatable about a pivot to translate the drive sleeve to move the first and second jaw members between the first and second positions, the pivot located a fixed distance above the longitudinal axis;
- a selectively moveable knife assembly having a knife bar which moves a knife to cut tissue between jaw members, the knife bar including a generally t-shaped proximal end dimensioned to operatively engage a corresponding slot defined within the housing, the slot guiding the movement of the knife bar during translation thereof; and
- a knife lockout mechanism operatively connected to the drive sleeve wherein translation of the drive sleeve moves the knife lockout mechanism from a first orientation in obstructive relationship with the knife bar to prevent movement thereof to a second orientation which allows selective, unencumbered movement of the knife bar to cut tissue disposed between the jaw members.

12. The endoscopic bipolar forceps according to claim 11, wherein the knife assembly includes a cuff at a distal end of the knife bar, the cuff dimensioned to encapsulate and move atop the drive sleeve upon movement of the knife bar.

13. The endoscopic bipolar forceps according to claim 12, further comprising a finger actuator operatively connected to the knife assembly, the finger actuator including two generally u-shaped flanges which rotate about a pivot to abut and force the cuff distally which, in turn, results in distal translation of the knife bar.

14. The endoscopic bipolar forceps according to claim 13, further comprising a spring which biases the cuff to force the knife assembly in a proximal-most orientation.

* * * * *